US007648827B2

(12) United States Patent
Echeverri et al.

(10) Patent No.: US 7,648,827 B2
(45) Date of Patent: Jan. 19, 2010

(54) USE OF EUKARYOTIC GENES AFFECTING CELL CYCLE CONTROL OR CELL CYCLE PROGRESSION FOR DIAGNOSIS AND TREATMENT OF PROLIFERATIVE DISEASES

(75) Inventors: Christophe Echeverri, Dresden (DE); Anthony Hyman, Dresden (DE); Pierre Gönczy, Lausanne (CH); Birte Sönnichsen, Dresden (DE); Steven Jones, Vancouver (CA); Andrew Walsh, Dresden (DE); Liisa Koski, Dresden (DE)

(73) Assignee: Cenix BioScience GmbH, Dresden (DE)

( * ) Notice: Subject to any disclaimer, the term of this patent is extended or adjusted under 35 U.S.C. 154(b) by 96 days.

(21) Appl. No.: 10/572,289

(22) PCT Filed: Sep. 15, 2004

(86) PCT No.: PCT/EP2004/010308

§ 371 (c)(1),
(2), (4) Date: Sep. 15, 2006

(87) PCT Pub. No.: WO2005/025624

PCT Pub. Date: Mar. 24, 2005

(65) Prior Publication Data

US 2007/0015161 A1    Jan. 18, 2007

Related U.S. Application Data

(60) Provisional application No. 60/502,651, filed on Sep. 15, 2003.

(51) Int. Cl.
*G01N 33/574* (2006.01)
(52) U.S. Cl. ..................... 435/7.23; 435/7.21
(58) Field of Classification Search ........................ None
See application file for complete search history.

(56) References Cited

U.S. PATENT DOCUMENTS

| 6,183,961 | B1 | 2/2001 | Bernstein et al. |
| 2003/0004120 | A1 | 1/2003 | McKay et al. |
| 2006/0014930 | A1 | 1/2006 | Garcia et al. |

FOREIGN PATENT DOCUMENTS

| WO | WO-95/24223 | 9/1995 |
| WO | WO-96/17933 | 6/1996 |
| WO | WO-99/32619 | 7/1999 |
| WO | WO-01/29221 | 4/2001 |
| WO | WO-03/011898 | 2/2003 |
| WO | WO-03/096964 | 11/2003 |

OTHER PUBLICATIONS

Montpetit et al, Eur J Hum Genetics, 2002, 10:62-71.*
Boehm, M., et al., "A Growth Factor-Dependent Nuclear Kinase Phosphorylates p27$^{Kip1}$ and Regulates Cell Cycle Progression", The EMBO Journal, 2002, vol. 21, No. 13, pp. 3390-3401.
The *C. elegans* Sequencing Consortium, "Genome Sequence of the Nematode *C. elegans*: A Platform for Investigating Biology", Science, 1998, vol. 282, pp. 2012-2018.
Feinberg, A. P., et al., "A Technique for Radiolabeling DNA Restriction Endonuclease Fragments to High Specific Activity", Analytical Biochemistry, 1983, vol. 132, pp. 6-13.
Fire, A., et al., "Potent and Specific Genetic Interference by Double-Stranded RNA in *Caenorhabditis elegans*", Nature, 1998, Vo. 391, pp. 806-811.
Gönczy, P. et al., "Dissection of Cell Division Processes in the One Cell Stage *Caenorhabditis elegans* Embryo by Mutational Analysis", The Journal of Cell Biology, 1999, vol. 144, No. 5, pp. 927-946.
Harris, D. M., et al., "The Arabidopsis Homolog of Yeast TAP42 and Mammalian α4 Binds to the Catalytic Subunit of Protein Phosphatase 2A and is Induced by Cilling", Plant Physiology, 1999, vol. 121, pp. 609-617.
Kirby, C., et al., "Mutations in the *par* Genes of *Caenorhabditis elegans* Affect Cytoplasmic Reorganization During the First Cell Cycle", Developmental Biology, 1990, vol. 142, pp. 203-215.
Maeda, K., et al., "The Gene Structure and Promoter Analysis of Mouse Lymphocyte Signal Transduction Molecule α4 that is Related to the Yeast TAP42 Involved in a Rapamycin-Sensitive Pathway", Gene, 1998, vol. 210, pp. 287-295.
Short, K. M., et al., "MID1 and MID2 Homo- and Heterodimerise to Tether the Rapamycin-Sensitive PP2A Regulatory Subunit, Alpha 4, to Microtubules: Implications for the Clinical Variability of X-Linked Opitz GBBB Syndrome and Other Developmental Disorders", BMC Cell Biology, 2002, vol. 3, No. 1, pp. 1-14.
Sulston, J. E., et al., "The Embryonic Cell Lineage of the Nematode *Caenorhabditis elegans*", Developmental Biology, 1983, vol. 100, pp. 64-119.
Tuschl, T., "Expanding Small RNA Interference", Nature Biotechnology, 2002, vol. 20, pp. 446-448.
Zhao, J., et al., "Identification of Transcription Factor KLF8 as a Downstream Target of Focal Adhesion Kinase in its Regulation of Cyclin D1 and Cell Cycle Progression", Molecular Cell, 2003, vol. 11, pp. 1503-1515.
Johnson, D., et al., "Hypothetical Protein F59E12.11", EMBL GenBank Accession No. O01902, Jul. 1, 1997.
"*Caenorhabditis elegans* cosmid F59E12, complete sequence", EMBL GenBank Accession No. AF003386, May 16, 1997.

* cited by examiner

*Primary Examiner*—Misook Yu
*Assistant Examiner*—Mark Halvorson
(74) *Attorney, Agent, or Firm*—Connolly Bove Lodge & Hutz LLP

(57) ABSTRACT

The present invention relates to the significant functional role of several *C. elegans* genes and of their corresponding gene products in cell cycle progression during cell division that could be identified by means of RNA-mediated interference (RNAi) and to the identification and isolation of functional orthologs of said genes including all biologically functional derivatives thereof. The invention further relates to the use of said genes and gene products (including said orthologs) in the development or isolation of anti-proliferative agents, particularly their use in appropriate screening assays, and their use for diagnosis and treatment of proliferative and other diseases. In particular, the invention relates to the use of small interfering RNAs derived from said genes for the treatment of proliferative diseases.

2 Claims, 8 Drawing Sheets

Fig. 1
F59E12.11

Fig. 2

CLUSTAL W (1.8) multiple sequence alignment

```
F59E12.11    MGNEQSSSTAGTSSNPQNQQSFSFLTRASTKRSKGIITVKDGNIPQEKLEDDEIYKRFT
NP_477517    MGSEQSSEAE----SRPNDLNSSVTPSPAKHRAKMDDIVVVAQGSQASRNVSNDPDVIKLQ
             *.****.:      *.*::.*:.:.***..:            ..  :*. ..:..:::*

F59E12.11    EIPRELPVIPAVIGKRDPQTNQGASYTHQKISSRPFFRLATRLQEHFAVNAKAVAADQAK
NP_477517    EIPTFQPLLKGLLSGQTSPTNA----KLEKLDSQQVLQLCLRYQDHLHQCAEAVAFDQNA
             ***  *::  .:: .:.. ***    *   : *: ::*  **  :*   . ****  **

F59E12.11    IPATCKSVEAKMIRLIEETRAHKEQHDGFMAALSGLNQLHDDICSIQIILEDIVPMVETL
NP_477517    LVKRIKEMDLSVETLFSFMQERQKRYAKYAEQIQKVNEMSAILRRIQMGIDQTVPLLDRL
             :  . *.: :: . :  :* :::. :  : . :.  ::: **: :*: **: :*::**

F59E12.11    NEILTPDERLPPLNLGSVLDRSPVPSSDSSLQSTPRHNQNIGHIDQIEPIEEIRVVDLPK
NP_477517    NSMLPEGERLEPEFSMK--------------------------------PD--RELRL---
             *::*  :***  :..                                 **::  * :
```

Fig. 4, 1/2

CLUSTAL W (1.8) multiple sequence alignment

```
NP_001542    --MAAEDELQLPRLPELFETGRQLLDEVEVATEPAGSRIVQEKVFKGLD-LLEKAAEMLS
AAD05364     -----EELLPRLPELFETSKKLLELEVATEPTGSRTIQDKVSKGLE-LLEKAAGMLS
Y71H2B.3     --MSELSDEEISLQALYDPSKKVIGDIEDGIFST--PELQPRIKTGID-NLQLVTKLVN
AAF53289     MAEGNTAGGEDQKLTDIFLKGWNIFDELEVTELPFNGSEFQNKVKTAMG-LFEQATVIVN
NP_013741    ---MASVTEQFNDIISLYS-T-----KLEHTSLRQDSPEYQGLLLSTIKKLLNLKTAIFD
                   : ::         :*      : :: :::.:

NP_001542    QLDLFSRNEDLEEIASTDIKYLLVPAFQGALTMKQVNPS-------------KRLDHLQRAREHF
AAD05364     QLDLFSRNEDLEEIASIDIKYIMVPALQGALTMKQVNPS-------------KRLDHLQRAREHF
Y71H2B.3     QMRLFSSNEQIEDVPTNSLPYLLVPCFIGILHQNLMTEPG------------LKLDELRKSKIYM
AAF53289     QVSMFSANELIDEVSTESLPFMLLPYFLGKLTTKINSPN-------------NTHSIELGEIYF
NP_013741    RLALFSTNETIDDVSTASIKELAVDYIYLGLLISRQSNDSDVAQRQSMKLIYIKKSVESF
             : :** **  ::::::: .: ::::. :       *     *    .:

NP_001542    INYLTQCHCYHVAEFELPKTMNNSAENHTANSSMAYP------------SLVAMASQRQAKIQRYK
AAD05364     IHFLTQCHCYHVAEFQLPQTKNNSAENNTARSSMAYP------------NLVAMASQRQAKIERYK
Y71H2B.3     RNFLDRLRDLCLITTRLPWEDEDTEEQNLKEK-------------------PKLAVEEITRLKLERHK
AAF53289     KDHLQRCQEYDLCAAPKSQVAKADSQAEKSEQR-------------------ELVEAAFNRNDKIAQYR
NP_013741    INFLTLLQDYKLLDPLVGEKLIGNFKDRYNPQLSELYAQPKNNKDLSGAQLKRKEKIELFQ
             :.* .*  ** ::::::: .: ::       *    .          *. *:   .::

NP_001542    QKKELEHRLSAMKSAVESGQAD---DERVREYYLLHLQRWIDISLEEIESIDQEIKILRE
AAD05364     QKKEVEHRLSALKSAVESGQAD---DERVREYYLLHLHRWIGISLEEIESIDQEIKILKD
Y71H2B.3     KKQELKMAELRIQKQLREAVSID---EQNLRELYITQLLFWSERCYEELQAIDDELPLLKM
AAF53289     RMKEIDEYMARMRDAVKNKTVD---DEDKRVFFLKYLDKSIIDSKQELETLGVMKQLAQM
NP_013741    RNKEISTKLHCLELELKNNDEDHDHDELLRELYLMRLHHFSLDTINNIEQNLFECEMLSN
             :*:   :      ::      .      ::::  .: ::::

NP_001542    RDS------------SREASTSNSSRQE-------------RPPVKPFIL
AAD05364     KDS------------PREESACQSSLPE-------------KPPMKPFIL
Y71H2B.3     MAERAS---------HPHRHPAPPATKT-------------VPTLKPFII
AAF53289     RLARLAGGESDNEVDSFRPPNQNQSSASSTSRGHGHSHGPGHHHHQQAAKPKPLQPFII
NP_013741    FLKNSVHEVKSSGTQIRKESNDDDSTGFTDKLEN-------INKPLIDKKGQVLRNFTL
                                                    :: *    .:

NP_001542    TRNMAQAKVFGAGYPSL-PTMTVSDWYEQHRKYGALPDQG-IAKAAPEEFRKAAQQQEEQ
AAD05364     TRNKAQAKVFGTGYPSL-ATMTVSDWYEQHQKYGALPDRG-IAKPPSADFEQRAAQQQEDQ
Y71H2B.3     TRDAQQKQVFGLGYPGI-PAMSVDEWYHQKFGHNPQNAPQ-SSAPAGAEAQESEEEVDDD
AAF53289     TRNATQKAVFGLGYPSL-PIMTVDEFYQQRVDEGIFPDEEKVAKMNQAQAIAAARDPNEK
NP_013741    VDKRQQLQQKVRGYGQYGPTMSVEEFLDKEFEEGRVLQGG------EEPEQAPDEENMDWQ
             *   **        .*:.:  .:            ..

NP_001542
AAD05364
Y71H2B.3
AAF53289
NP_013741
```

Fig. 4, 2/2

CLUSTAL W (1.8) multiple sequence alignment (Con't)

```
NP_001542    EEKEEEDDEQ---------------TLHRAR-------------------------
AAD05364     SKRMKRMRRKPCTGCESGMTGRTRIPGAMATGR------------------------
Y71H2B.3     EARAKAMR-------------------------------------------------
AAF53289     EDEEKAVEELQAEQDDPEYIDRMRRMDEYKDVQPKSRMSVRDFIKGLPIHDSSNFTHLSN
NP_013741    DRETYKAR-------------------------------------------------

NP_001542    ----------------------------------------EWDDW----KDTHPRGYGNR
AAD05364     ------------------------------------------------TWASHSRRPKDNVHTFTPR
Y71H2B.3     ----------------------------------------WDEY-----KDDHRRGWGNM
AAF53289     EHGIRTSQKRASVYLPTEDEHSEQLIVMDKRCVLLRYLTQQWDKKTLQRKREHGGDSGNG
NP_013741    ----------------------------------------EWDEF----KESHAKGSGNT
                                                     *        *

NP_001542    QNMG--------------------------
AAD05364     TTSGGCSEGSHVESCIAFDSVK--------
Y71H2B.3     HNKG--------------------------
AAF53289     NGNSSTPNGNSTNSKKRPRLDPNELN
NP_013741    MNRG--------------------------
```

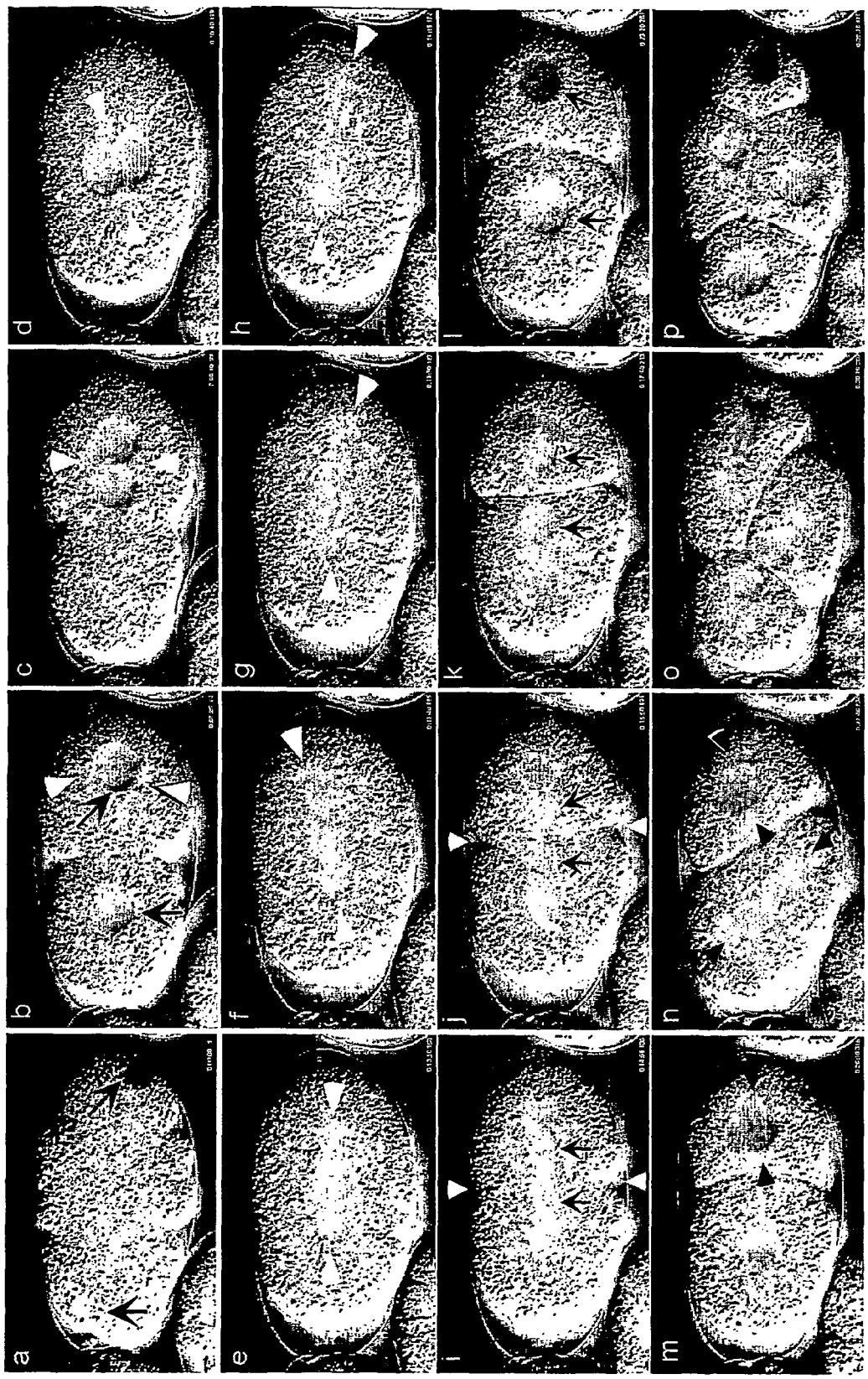
Fig. 5 Wild type

USE OF EUKARYOTIC GENES AFFECTING CELL CYCLE CONTROL OR CELL CYCLE PROGRESSION FOR DIAGNOSIS AND TREATMENT OF PROLIFERATIVE DISEASES

RELATED APPLICATIONS

This application is a national stage application (under 35 U.S.C. 371) of PCT/EP2004/010308 filed Sep. 15, 2004 which claims benefit to U.S. provisional application 60/502,651 filed Sep. 15, 2003.

The present invention relates to the use of agents interfering with cell cycle control or cell cycle progression for the treatment of diseases, especially proliferative diseases.

Metazoan cell division (mitosis) consists of an extremely complex, highly regulated set of cellular processes which must be tightly co-ordinated, perfectly timed, and closely monitored in order to ensure the correct delivery of cellular materials to daughter cells. Defects in these processes are known to cause a wide range of so-called proliferative diseases, including all forms of cancer. Since cell division represents one of the few, if not the only cellular process that is common to the aetiology of all forms of cancer, its specific inhibition has long been recognised as a preferred site of therapeutic intervention.

Although mitotic inhibitor drugs are recognised as one of the most promising classes of chemotherapeutic agents, screening attempts to find new drug candidates in this class have been undermined by the strong inherent tendency of such screens to identify agents that target a single protein, tubulin. Tubulin polymerises to form microtubules, the primary cytoskeletal elements needed for mitotic spindle function and chromosome segregation. Microtubules as such, however, are ubiquitously needed in almost all cell types, whether dividing or not, a fact which therefore explains many of the unwanted side effects caused by anti-tubulin drugs.

Perhaps the best known example of a highly successful anti-neoplastic drug that targets tubulin is paclitaxel, and its marketed derivative, Taxol. Its applicability has indeed been seriously limited by difficulties in determining an adequate dosing regimen due to a range of problematic side effects. Taxol treatment has resulted in anaphylaxis and severe hypersensitivity reactions characterised by dyspnea and hypotension requiring treatment, angioedema, and generalised urticaria in 2-4% of patients in clinical trials. Although Taxol is administered after pretreatment with corticosteroids, fatal reactions have occurred. Severe conductance abnormalities resulting in life-threatening cardiac arrhythmia occur in less than 1 percent of patients and must be treated by insertion of a pacemaker. Taxol can cause fetal harm or fetal death in pregnant women. Furthermore, administration is commonly accompanied by tachycardia, hypotension, flushing, skin reactions and shortness-of-breath (mild dyspnea). Reasons for these strong side-effects may be that since tubulin does not only play an essential role in spindle formation, but also plays significant roles in other cellular processes like for instance cytoskeleton generation and intracellular protein transport Consequently, although Taxol has been hailed by many as the most successful new anti-cancer therapeutic of the last three decades, there is still a need for anti-cancer drugs that do not show the disadvantages of Taxol.

Therefore, the problem underlying the present invention resides in providing improved potent anti-cancer drugs, particularly with less severe side effects.

The problem is solved by the use of an isolated nucleic acid molecule comprising a sequence selected from the group of sequences consisting of:
a) the nucleic acid sequences presented in SEQ ID NO. 5, 7, 9, 11, 13, 1, 3;
b) nucleic acid sequences encoding polypeptides that exhibit a sequence identity with the protein encoded by a nucleic acid according to a) of at least 25% over 100 residues and/or which are detectable in a computer aided search using the BLAST sequence analysis programs with an e-value of at most $10^{-5}$,
c) sequences of nucleic acid molecules which are capable of hybridizing with the nucleic acid molecules with sequences corresponding to (a) or (b) under conditions of medium or high stringency,
d) the antisense-sequence of any of the sequences as defined in (a), (b) or (c),
e) fragments of (a), (b), (c) or (d),
f) double-stranded RNA or single-stranded RNA in the antisense or sense direction corresponding to any of the sequences as defined in (a), (b), (c), (d), or (e) for the manufacture of a medicament for the inhibition of cell cycle progression.

The present invention is based on the concept to provide agents interfering with cell cycle progression. Cell cycle progression is an essential part of cell division.

Since cell cycle progression—in contrast to microtubule formation—is a cell division-specific process, the inhibition of target proteins involved in cell cycle progression results in an efficient impairment of mitosis as well as in a reduced number of side effects caused by the inhibition of other significant cellular processes.

The present invention discloses for the first time for a variety of proteins and genes that they are involved in cell cycle progression. Although cell division and cell cycle progression have already been thoroughly studied, the present invention provides several classes of target genes, corresponding gene products and other agents that had previously not been implicated in cell division, particularly not in cell cycle progression. The newly identified function of these target genes and their corresponding gene products, any homologs, orthologs and derivatives thereof enables their use in the development of a wide range of medicaments against proliferative diseases including cancer. These medicaments could be used in treatment of proliferative diseases, particularly in those cases where the disorder relates to cell division, regulation of cell division, or is dependent on cell cycle control or cell cycle progression. Furthermore, the newly identified function enables the use in diagnosis and the development of diagnostic agents.

For the identification of target genes being involved in cell cycle control or cell cycle progression, a large-scale RNAi technique-based screen was performed for 19514 (that means 99.7%) of the predicted open reading frames in the *C. elegans* genome. For the performance of this large-scale screen double-stranded RNA corresponding to the individual open reading frames was produced and micro-injected into adult *C. elegans* hermaphrodites, and the resulting embryos were analysed 24 hours later using time-lapse DIC microscopy.

The nematode *C. elegans* exhibits an almost entirely translucent body throughout its development, thereby offering unparalleled microscopic access for exquisitely detailed cytological documentation, even for the earliest steps of embryogenesis. This important feature, along with its short life cycle (3-5 days), its ease of cultivation, and its low maintenance costs, has helped make *C. elegans* arguably the best studied of all metazoans. Also, sequence data are now available for over 97% of the *C. elegans* genome (*C. elegans* Sequencing Consortium. Genome sequence of the nematode *C. elegans*: a platform for investigating biology. Science 282, 2012-2018 (1998)). Thus, *C. elegans* is an ideal organism for applying the new technique of RNA-mediated interference (RNAi). This technique consists in the targeted, sequence-specific inhibition of gene expression, as mediated by the introduction into an adult worm of double-stranded RNA (dsRNA) molecules corresponding to portions of the coding sequences of interest (Fire et al., Potent and specific genetic interference by double-stranded RNA in *Caenorhabditis elegans*. Nature 391, 806-811 (1998)). For the vast majority of *C. elegans* genes tested to date, this has been shown to yield a sequence-specific inhibition of the targeted gene's expression, accompanied by clearly detectable loss of function phenotypes in the treated worm's F1 progeny (and even in some cases, in the treated worm itself).

In the context of the present invention, a screening assay in *C. elegans* based on 'genomic RNA mediated interference (RNAi)' combined with a highly probative microscopic assay for documenting the first rounds of embryonic cell division was used (Sulston et al., The embryonic cell lineage of the nematode *Caenorhabditis elegans*. Dev. Biol. 100, 64-119 (1983); Gönczy et al., Dissection of cell division processes in the one cell stage *Caenorhabditis elegans* embryo by mutational analysis. J Cell Biol 144, 927-946 (1999)). With this combination of techniques a selected gene and also a variety of selected genes can be functionally characterized with unprecedented speed and efficiency.

The DIC microscopy generated movies were analyzed to identify those samples whereby cell division was altered or disrupted. In order to perform the analysis in a robust, consistent and reproducible fashion, each movie was analyzed with regard to 47 different parameters. In other words, 47 features of normal cell division (i.e. cell division in wild type worms) were scored for every RNAi phenotype generated by the genome-wide application of RNAi across the entire *C. elegans* genome.

A powerful confirmation and validation of the DIC assay, and the depth of information that the assays yield, was that equivalent phenotypes were found to represent closely related proteins, proteins within the same family or functionally equivalent proteins. In other words, if the RNAi-induced phenotypes of two separately analyzed genes are the same, it is very likely that the two proteins are either within the same protein class or share a similar function or at the very least, are both involved in the same biological mechanism or process. Therefore, the screen can be used to class or group proteins according to their function. Consequently, any genes that give rise to similar RNAi phenotypes are related and are justified to be considered within single functional classes.

"Nucleic acids" according to the present invention comprises all known nucleic acids such as DNA, RNA, peptide nucleic acids, morpholinos, and nucleic acids with backbone structures other than phosphodiesters, such as phosphothiates or phosphoramidates.

"inhibition of cell cycle progression" according to the present invention includes halting or arresting as well as retarding or slowing down of cell cycle progression. Particularly, "inhibition of cell cycle progression" relates to an arrest, retardation or slowing down of cell cycle progression at an early stage, preferably before nuclear division and particularly before division of the cytoplasm (cytokinesis).

In a preferred embodiment of the invention, the nucleic acid molecule comprises a nucleic acid molecule with a sequence selected from the group of sequences as presented in SEQ ID NO. 5, 7, 9, 11, 13, 1, 3. Preferably, the nucleic acid molecule consists of a nucleic acid molecule with a sequence selected from said group of sequences.

The term "comprise" preferably refers to nucleic acids in which the nucleic acids with the described sequences are functionally relevant, e.g. for diagnostic use or therapeutic use, such as vectors for therapeutical use or expression of corresponding RNAs or proteins. Preferably, any additional nucleic acids upstream or downstream of the sequence are not longer than 20 kb. More preferred, the term "comprise" does not relate to large constructs accidentally including the sequence, such as genomic BAC or YAC clones.

In detail, the individual SEQ ID No. denotes the following sequences:

SEQ ID NO. 1 the nucleotide sequence of the *C. elegans* gene F59E12.11 (Wormbase accession No. CE28570)

SEQ ID NO. 2 the deduced amino acid sequence of the *C. elegans* gene F59E12.11 (accession No. CE28570)

SEQ ID NO. 3 the nucleotide sequence of the human ortholog of F59E12.11 (GenBank accession No. NM_058169)

SEQ ID NO. 4 the deduced amino acid sequence of the human ortholog of F59E12.11 (GenBank accession No. NP_477517)

SEQ ID NO. 5 the nucleotide sequence of the *C. elegans* gene Y71H2B.3 (Wormbase accession No. CE24630)

SEQ ID NO. 6 the deduced amino acid sequence of the *C. elegans* gene Y71H2B.3 (Wormbase accession No. CE24630)

SEQ ID NO. 7 the nucleotide sequence of the human ortholog of Y71H2B.3 (GenBank accession No. NM_001551)

SEQ ID NO. 8 the deduced amino acid sequence of the human ortholog of Y71H2B.3 (GenBank accession No. NP_001542)

SEQ ID NO. 9 the nucleotide sequence of the rat ortholog of Y71H2B.3 (GenBank accession No. NM_031624)

SEQ ID NO. 10 the deduced amino acid sequence of the rat ortholog of Y71H2B.3 (GenBank accession No. AAD05364 or NP_113812)

SEQ ID NO. 11 the nucleotide sequence of the *Drosophila* ortholog of Y71H2B.3 (GenBank accession No. AAF003639)

SEQ ID NO. 12 the deduced amino acid sequence of the *Drosophila* ortholog of Y71H2B.3 (GenBank accession No. AAF53289)

SEQ ID NO. 13 the nucleotide sequence of the yeast ortholog of Y71H2B.3 (GenBank accession No. NC_001145, base pairs 327481 to 328581)

SEQ ID NO. 14 the deduced amino acid sequence of the yeast ortholog of Y71H2B.3 (GenBank accession No. NP_013741)

Unless otherwise specified, the manipulations of nucleic acids and polypeptides/-proteins can be performed using standard methods of molecular biology and immunology (see, e.g. Maniatis et al. (1989), Molecular cloning: A laboratory manual, Cold Spring Harbor Lab., Cold Spring Harbor, N.Y.; Ausubel, F. M. et al. (eds.) "Current protocols in Molecular Biology". John Wiley and Sons, 1995; Tijssen, P., Practice and Theory of Enzyme Immunoassays, Elsevier Press, Amsterdam, Oxford, N.Y., 1985).

The present invention describes genes identified as having essential functions in cell division in the model organism *C. elegans*. The basis for performing research in model organisms is that the newly discovered functions for the genes in *C. elegans* will be conserved in other species including humans. Cell division as well as cell cycle control and progression are highly conserved during evolution and therefore the approach of discovering a gene function in *C. elegans* and using the information to characterise or assign functions for human homologs or orthologs is well justified.

One theme of conservation is that the gene function can be conserved with substantial divergence of sequence. In the present invention this theme of conservation is not defined. However, if other genes are discovered to have functions that result in the gene product being identified as the same gene product as those claimed in the present invention then the present claims also apply to such genes.

However, the most frequent theme of conservation of genes during evolution is that the gene sequence is conserved. This theme of conservation is particularly frequent for genes involved in highly conserved processes such as cell division. This means that the DNA nucleotide sequence or the protein coding sequence of the gene are very similar in different species, which in turn suggests that the function of the gene is the same in the different species.

Therefore, in a further preferred embodiment, the nucleic acid molecule has a sequence that encodes a polypeptide exhibiting a sequence identity with a protein encoded by SEQ ID NO. 5, 7, 9, 11, 13, 1, 3 of at least 25% over 100 residues, preferably of at least 30% over 100 residues, more preferably of at least 50% over 100 residues, particularly of at least 70% over 100 residues on amino acid level.

These very high sequence similarities are usually shown by polypeptides which are orthologs or homologs of the above sequences. A homolog is a protein with similar sequence from the same or another species (an homolog's sequence similarity originates from a speciation event or from a gene duplication, i.e. a homolog is a related protein in any species or the same protein in another species). A subgroup of homologs are defined as orthologs. An ortholog is essentially the same protein as the one it is compared to, but it is derived from another species (an ortholog's sequence similarity originates from a speciation event rather than a gene duplication). It is known to a person skilled in the art, that in a conserved process such as cell division, homologous and orthologous proteins, particularly orthologous proteins, are very likely to serve the same biological function. In the present case, the most relevant biological function is the involvement in, particularly the requirement for, cell cycle control or progression.

Advantageously, it could already be shown that human orthologs of the C.elegans genes identified in the context of this invention are required for proliferation, cell survival and mitosis (see Example 6). This finding indicates that the human orthologs are required for cell cycle control or progression and can be used in the context of diagnosis and treatment of proliferative diseases.

The person skilled in the art is familiar with different methods and criteria to identify homologs and orthologs. In the context of the present invention, homologs and orthologs were identified based on sequence similarity according to the procedure described in Example 1.

The nucleic acid molecule may also comprise a sequence that is detectable in a computer aided database search/alignment with an e-value of at most $10^{-5}$, preferably with an e-value of at most $10^{-12}$, particularly with an e-value of at most $10^{-20}$ or fragments thereof whereby the database sequences are compared to the sequences as defined under a). The nucleic acid molecule may also comprise a sequence that is considered an ortholog according to the criteria of the present invention (see Example 1). Generally, the grade of sequence identity can be calculated by any software program that is capable to perform protein sequence alignments known in the art. Hereby it is also included that identical amino acid regions are interrupted by gaps that can be variable in their length.

For this kind of analysis or alignments the "BLAST sequence analysis programs" are particularly preferred. The "BLAST sequence analysis programs" which may be used for sequence analysis are publically available and known to anyone skilled in the art. Known analysis programs for sequence alignments, particularly the "BLAST sequence analysis programs", calculate so called "e-values" to characterize the grade of homology between the compared sequences. Generally, a small e-value characterizes a high sequence similarity, whereas larger e-values characterize lower sequence similarity.

The degree of similarity required for the sequence variant will depend upon the intended use of the sequence. It is well within the capability of a person skilled in the art to effect mutational, insertional and deletional mutations which are designed to improve the function of the sequence or otherwise provide a methodological advantage.

The aforementioned grades of sequence identities with proteins encoded by the above SEQ IDs are characteristic for such polypeptides that are strongly homologous to the above sequences, in particular for polypeptides that are "orthologous" or "homologous" to the polypeptides of a).

Table 1 shows the e-values that have been calculated for the alignments on amino acid level with homologs and orthologs of the corresponding C. elegans gene. Hereby, e-values lower than $10^{-5}$ on amino acid level characterize homologs of the corresponding C. elegans genes. If the C. elegans gene is itself a reciprocal hit of the identified homolog with an e-value of less than $10^{-5}$, then the homolog is identified as an ortholog (see also Example 1).

TABLE 1

Sequence similarities between the C. elegans genes F59E12.11, Y71H2B.3 and their human, rat, Drosophila, and yeast homologs and orthologs.

| C. elegans gene | e-value for the alignment with the C. elegans gene on amino acid level |
|---|---|
| F59E12.11 | Human ortholog 1 * $10^{-7}$ |
| Y71H2B.3 | Human ortholog 1 * $10^{-39}$ |
|  | Rat ortholog 2 * $10^{-31}$ |
|  | Drosoph. ortholog 1 * $10^{-21}$ |
|  | Yeast ortholog 3 * $10^{-13}$ |

According to a further preferred embodiment, the nucleic acid molecule comprises a nucleotide sequence which is capable of hybridizing with the nucleic acid sequences of (a) or (b) under conditions of medium/high stringency.

In such hybrids, duplex formation and stability depend on substantial complementarity between the two strands of the hybrid and a certain degree of mismatch can be tolerated. Therefore, the nucleic acid molecules and probes of the present invention may include mutations (both single and multiple), deletions, insertions of the above identified sequences, and combinations thereof, as long as said sequence variants still have substantial sequence similarity to the original sequence which permits the formation of stable hybrids with the target nucleotide sequence of interest.

Suitable experimental conditions for determining whether a given DNA or RNA sequence "hybridizes" to a specified polynucleotide or oligonucleotide probe involve presoaking of the filter containing the DNA or RNA to examine for hybridization in 5×SSC (sodium chloride/sodium citrate) buffer for 10 minutes, and prehybridization of the filter in a solution of 5×SSC, 5× Denhardt's solution, 0.5% SDS and 100 mg/ml of denatured sonicated salmon sperm DNA (Maniatis et al., 1989), followed by hybridization in the same solution containing a concentration of 10 ng/ml of a random primed (Feinberg, A. P. and Vogelstein, B. (1983), Anal. Biochem. 132:6-13), $^{32}$P-dCTP-labeled (specific activity>1×10$^9$ cpm/µg) probe for 12 hours at approximately 45° C. The filter is then washed twice for 30 minutes in 2×SSC, 0.5% SDS at at least 55° C. (low stringency), at least 60° C. (medium stringency), preferably at least 65° C. (medium/high stringency), more preferably at least 70° C. (high stringency) or most preferably at least 75° C. (very high stringency). Molecules to which the probe hybridizes under the chosen conditions are detected using an x-ray film or a "phosphor imager".

According to a further preferred embodiment, the nucleic acid molecules may also have the antisense-sequence of any of the sequences as defined in (a), (b) or (c).

According to a further preferred embodiment, fragments of the nucleic acid molecules as described above may be used.

The term "fragment" as used according to the present invention can have different meanings depending on the molecule and purpose referred to. A person skilled in the art knows how to choose appropriate fragments for the relevant purpose. Preferably, a fragment should be specific for the sequence it is derived from. The meaning of the term "specific" is known in the art. Preferably, specific in this context means that in a BLAST search performed with the sequence fragment, the original sequence (from which the fragment is derived) would be identified with a lower e-value than all other sequences relevant in the context of the current use (e.g. all other sequences of nucleic acids present in the investigated sample). More preferably, the original sequence should be identified with the lowest e-value compared to all other sequences identified. Alternatively, "specific" means that, under the applied conditions, the fragment binds only to the nucleic acid molecule it is derived from. The criterion of specificity is usually achieved by fragments larger than 15 nucleotides, preferably larger than 19 nucleotides. Preferably, the fragments are chosen from sequence regions of high complexity. Low complexity regions can be identified by database searches or low complexity filters available in standard sequence analysis programs. "Biologically active" fragments or derivatives can be generated by a person skilled in the art. Hereby, the fragments or derivatives should have a similar "biological function" as the nucleic acid they are derived from. According to the present invention the most relevant biological function is the involvement in, inhibition of, activation of, or requirement for cell cycle control, particularly for cell cycle progression.

The isolated nucleic acid molecules defined as under (a) to (e) may be used for influencing cell division and/or cell proliferation, particularly by inhibiting cell cycle progression, either in vitro or in vivo.

Inhibition of cell cycle progression using said nucleic acid molecules can be achieved by different ways familiar to the person skilled in the art. For example, the isolated nucleic acid molecules may be inserted downstream of a strong promotor to overexpress the corresponding protein or polypeptide. Overexpression of the protein or polypeptide may lead to suppression of the endogenous protein's biological function. By introducing deletions or other mutations into the nucleic acids, or by using suitable fragments, it is possible to generate sequences encoding dominant-negative peptides or polypeptides. Such dominant-negative peptides or polypeptides can inhibit the function of the corresponding endogenous protein.

Certain nucleic acids can be used to inhibit expression (transcription and/or translation) of the endogenous genes to inhibit cell cycle progression. E.g. peptide nucleic acids comprising sequences as identified above can suppress expression of the corresponding endogenous gene by forming DNA triplex structures with the gene. Other nucleic acids, such as antisense morpholino oligonucleotides or ribozymes, can be used to interfere with RNA transcribed from the endogenous gene.

The application of automated gene synthesis provides an opportunity for generating sequence variants of the naturally occurring genes. It will be appreciated that polynucleotides coding for synthetic variants of the corresponding amino acid sequences can be generated which, for example, will result in one or more amino acids substitutions, deletions or additions. Also, nucleic acid molecules comprising one or more synthetic nucleotide derivatives (including morpholinos) which provide said nucleotide sequence with a desired feature, e.g. a reactive or detectable group, can be prepared. Synthetic derivatives with desirable properties may also be included in the corresponding polypeptides. All such derivatives and fragments of the above identified genes and gene products showing at least part of the biological activity or biological function of the naturally occurring sequences or which are still suitable to be used, for example, as probes for, e.g. identification of homologous genes or gene products, are included within the scope of the present invention. Also included are such derivatives and fragments whose activity or function is counteracting to the biological activity or biological function of the naturally occurring sequences, e.g. derivatives and fragments that encode dominant-negative molecules.

Having herein provided the nucleotide sequences of various genes functionally involved in cell cycle control, particularly cell cycle progression, it will be appreciated that automated techniques of gene synthesis and/or amplification may be used to isolate said nucleic acid molecules in vitro. Because of the length of some coding sequences, application of automated synthesis may require staged gene construction, in which regions of the gene up to about 300 nucleotides in length are synthesized individually and then ligated in correct succession for final assembly. Individually sythesized gene regions can be amplified prior to assembly, using polymerase chain reaction (PCR) technology. The technique of PCR amplification may also be used to directly generate all or part of the final genes/nucleic acid molecules. In this case, primers are synthesized which will be able to prime the PCR amplification of the final product, either in one piece or in several pieces that may be ligated together. For this purpose, either cDNA or genomic DNA may be used as the template for the PCR amplification. The cDNA template may be derived from commercially available or self-constructed cDNA libraries.

According to a further preferred embodiment, the invention relates to the use of the above identified nucleic acid molecules or fragments thereof in form of RNA, particularly antisense RNA and double-stranded RNA, for the manufacture of a medicament for the inhibition of cell cycle progression. Also ribozymes can be generated for the above identified sequences and used to degrade RNA transcribed from the corresponding endogenous genes.

As stated above, double-stranded RNA oligonucleotides effect silencing of the expression of gene(s) which are highly homologous to either of the RNA strands in the duplex. Recent discoveries had revealed that this effect, called RNA interference (RNAi), that had been originally discovered in *C. elegans,* can also be observed in mammalian, particularly in human cells. Thus, inhibition of a specific gene function by RNA interference can also be performed in mammalian cells, particularly also in human cells.

As shown in FIG. 1, the inhibition of a nucleic acid molecule as defined under (a) to (f) by RNAi in *C. elegans* inhibits cell division by impairing cell cycle progression.

Particularly preferred is the use of these RNA molecules in a therapeutical application of the RNAi technique, particularly in humans or in human cells.

An RNAi technique particularly suited for mammalian cells makes use of double-stranded RNA oligonucleotides known as "small interfering RNA" (siRNA).

Therefore, according to a further preferred embodiment, the invention relates to the use of nucleic molecules comprising small interfering RNA with a sequence corresponding to any of the sequences identified above.

These siRNA molecules can be used for the therapeutical silencing of the expression of the genes of the invention comprising nucleic acid sequences as defined under (a) to (f), in mammalian cells, particularly in human cells, particularly for the therapy of a proliferative disease.

The inhibition of a specific target gene in mammals is achieved by the introduction of an siRNA-molecule having a sequence that is specific (see above) for the target gene into the mammalian cell. The siRNAs comprise a first and a second RNA strand, both hybridized to each other, wherein the sequence of the first RNA strand is a fragment of one of the sequences as defined in a) to f) and wherein the sequence of the second RNA strand is the antisense-strand of the first RNA strand. The siRNA-molecules may possess a characteristic 2- or 3-nucleotide 3'-overhanging sequence. Each strand of the siRNA molecule preferably has a length of 19 to 31 nucleotides.

The siRNAs can be introduced into the mammalian cell by any suitable known method of cell transfection, particularly lipofection, electroporation or microinjection. The RNA oligonucleotides can be generated and hybridized to each other in vitro or in vivo according to any of the known RNA synthesis methods.

The possibility to inhibit gene expression of disease-associated genes also in mammalian cells and in particular in human cells, make siRNAs or vector systems capable of producing siRNAs, having the sequence of those disease-associated genes, an interesting therapeutical agent for pharmaceutical compositions. Particularly siRNAs having sequences as defined in the present invention or that are homologous or orthologous to one of those genes can be used for the manufacture of medicaments for the inhibition of cell cycle progression and for the therapy of diseases, particularly proliferative diseases. Similarly, nucleic acid vectors capable of producing those siRNAs can be used for the manufacture of such medicaments.

In another embodiment, the invention relates to the use of a nucleic acid molecule as defined above, wherein the nucleic acid molecule is contained in at least one nucleic acid expression vector which is capable of producing a double-stranded RNA-molecule comprising a sense-RNA-stand and an antisense-RNA-strand under suitable conditions, wherein each RNA-strand, independently from the other, has a length of 19 to 31 nucleotides.

In this alternative method (also described in Tuschl, Nature Biotechnology, Vol. 20, pp. 446-448), vector systems capable of producing siRNAs instead of the siRNAs themselves are introduced into the mammalian cell for downregulating gene expression.

The preferred lengths of the RNA-strands produced by such vectors correspond to those preferred for siRNAs in general (see below).

"Suitable conditions" for the production of the above double-stranded RNA-molecule are all in vivo or in vitro conditions that according to the state of art allow the expression of a first and a second RNA-strand with the above sequences and lengths that—when hybridized—form a double-stranded RNA-molecule. Particularly preferred "suitable conditions" for the production of the above double-stranded RNA-molecule are the "in vivo conditions" in a living human or animal cell or the "in vitro conditions" in cultured human or animal cells.

The "nucleic acid expression vector" may be an extrachromosomal entity, the replication of which is independent of chromosomal replication, e.g. a plasmid. Alternatively, the vector may be one which, when introduced into a host cell, particularly into a mammalian host cell, is integrated into the host cell genome and replicated together with the chromosome(s) into which it has been integrated. Preferably, the "nucleic acid expression vector" may be an expression vector which is usually applied in gene therapeutic methods in humans, particularly a retroviral vector or an adenoviral vector.

The coding sequence of interest may, if necessary, be operably linked to a suitable terminator or to a polyadenylation sequence. In the case of RNA, particularly siRNA, "coding sequence" refers to the sequence encoding or corresponding to the relevant RNA strand or RNA strands.

Further, the vector may comprise a DNA sequence enabling the vector to replicate in the mammalian host cell. Examples of such a sequence—particularly when the host cell is a mammalian cell—is the SV40 origin of replication.

A number of vectors suitable for expression in mammalian cells are known in the art and several of them are commercially available. Some commercially available mammalian expression vectors which may be suitable include, but are not limited to, pMC1neo (Stratagene), pXT1 (Stratagene), pSG5 (Stratagene), pcDNAI (Invitrogen), EBO-pSV2-neo (ATCC 37593), pBPV-1(8-2) (ATCC 37110), pSV2-dhfr (ATCC 37146). Preferred are all suitable gene therapeutic vectors known in the art.

In a particularly preferred embodiment of the invention the vector is a retroviral vector. Retroviruses are RNA-viruses possessing a genome that after the infection of a cell, such as a human cell, is reversely transcribed in DNA and subsequently is integrated into the genome of the host cell. Retroviruses enter their host cell by receptor-mediated endocytosis. After the endocytosis into the cell the expression of the retroviral vector may be silenced to ensure that only a single cell is infected. The integration of the viral DNA into the genome is mediated by a virus-encoded protein called integrase, wherein the integration locus is not defined. Retroviral vectors are particularly appropriate for their use in gene therapeutic methods, since their transfer by receptor-mediated endocytosis into the host cell, also known to those skilled in the art as "retroviral transduction" is particularly efficient A person skilled in the art also knows how to introduce such retroviral vectors into the host cell using so called "packaging cells".

In another particularly preferred embodiment of the invention, the vector is an adenoviral vector or a derivative thereof Adenoviral vectors comprise both replication-capable and and replication-deficient vectors. The latter include vectors deficient in the E1 gene.

The recombinant vector is preferably introduced into the mammalian host cells by a suitable pharmaceutical carrier that allows transformation or transfection of the mammalian, in particular human cells. Preferred transformation/transfection techniques include, but are not limited to liposome-mediated transfection, virus-mediated transfection and calcium phosphate transfection.

In a preferred embodiment, the invention relates to the use of a vector system capable of producing siRNAs as defined above, wherein the nucleic acid corresponding to the siRNA is contained in at least one nucleic acid expression vector comprising a first expression cassette containing the nucleic acid corresponding to the sense-RNA-strand under the control of a first promoter and a second expression cassette containing the nucleic acid corresponding to the antisense-RNA-strand under the control of a second promoter.

In the above mentioned vector system, the vector comprises two individual promoters, wherein the first promoter controls the transcription of the sense-strand and the second promoter controls the transcription of the antisense strand (also described in Tuschl, Nature Biotechnology, Vol. 20, pp. 446-448). Finally the siRNA duplex is constituted by the hybridisation of the first and the second RNA-strand.

The term "expression cassette" is defined herein to include all components which are necessary or advantageous for the expression of a specific target polypeptide. An "expression cassette" may include, but is not limited to, the nucleic acid sequence of interest itself (e.g. encoding or corresponding to the siRNA or polypeptide of interest) and "control sequences". These "control sequences" may include, but are not limited to, a promoter that is operatively linked to the nucleic acid sequence of interest, a ribosome binding site, translation initiation and termination signals and, optionally, a repressor gene or various activator genes. Control sequences are referred to as "homologous", if they are naturally linked to the nucleic acid sequence of interest and referred to as "heterologous" if this is not the case. The term "operably linked" indicates that the sequences are arranged so that they function in concert for their intended purpose, i.e. expression of the desired protein, or, in case of RNA, transcription of the desired RNA.

The promoter used in the aforementioned "expression cassettes" may be any DNA sequence which shows transcriptional activity in a host cell of choice, preferably in a mammalian host cell, particularly in a human host cell. The promoter may be derived from genes encoding proteins either homologous or heterologous to the host cell.

As a promoter in general every promoter known in the prior art can be used that allows the expression of the gene of interest under appropriate conditions in a mammalian host cell, in particular in a human host cell. Particularly promoters derived from RNA polymerase III transcription units, which normally encode the small nuclear RNAs (snRNAs) U6 or the human RNAse P RNA H1, can be used as promoters to express the therapeutic siRNAs. These particularly preferred promoters U6 and H1 RNA which are members of the type III class of Polymerase III promoters are—with the exception of the first transcribed nucleotide (+1 position)—only located upstream of the transcribed region.

In a preferred embodiment, the invention relates to the use of a vector system capable of producing siRNAs for the above identified nucleic acid sequences, wherein the sequence is contained in at least one nucleic acid expression vector comprising an expression cassette containing the sequence of the sense-RNA-strand and of the antisense-RNA-strand under the control of a promoter leading to a single-stranded RNA-molecule and wherein the single-stranded RNA-molecule is capable of forming a back-folded stem-loop-structure.

In this vector system (also described in Tuschl, Nature Biotechnology, Vol. 20, pp. 446-448), only a single RNA-strand is produced under the control of a single promoter, wherein the RNA strand comprises both the sense- and of the antisense-strand of the final double-stranded siRNA molecule. This structure leads to a back-folding of the RNA-strand by hybridisation of the complementary sense- and antisense-sequences under stem-loop formation. Finally the intracellular processing of this fold-back stem-loop-structure gives rise to siRNA.

In another preferred embodiment according to the present invention, the "nucleic acid expression vector" comprises an expression cassette containing the sequence of the sense-RNA-strand and of the antisense-RNA-strand both under the control of a single promoter leading to a single-stranded RNA-molecule. This single-stranded RNA-molecule is hereby capable to form a back-folded stem-loop-structure. These expressed "hairpin RNA-molecules" subsequently give rise to siRNAs after intracellular processing.

In a preferred embodiment of the invention the nucleic acid expression vector that gives rise to the expression of siRNAs according to the present invention is first introduced into therapeutic, non-toxic virus particles or virus-derived particles that are suitable for gene therapeutic applications and that can infect mammalian, in particular human target cells, such as packaging cells etc.

In a preferred embodiment, the first and the second RNA strand of the siRNA may have, independently from the other, a length of 19 to 25 nucleotides, more preferred of 20 to 25 nucleotides, and most preferred of 20 to 22 nucleotides.

In another preferred embodiment, the first and the second RNA strand of the siRNA may have, independently from the other, a length of 26 to 30 nucleotides, more preferred of 26 to 28 nucleotides, and most preferred of 27 nucleotides.

The present invention also relates to the use of and/or methods involving proteins, polypeptides and peptides encoded by the above defined sequences.

In another aspect, the invention relates to the use of isolated proteins or polypeptides comprising a sequence of the group selected of:

(a) a sequence as disclosed in SEQ ID NO. 6, 8, 10, 12, 14, 2, 4;

(b) a sequence that exhibits a sequence identity with any of the sequences according to (a) of at least 25% over 100 residues, (c) or fragments of the sequences defined in (a) or (b), for the manufacture of a medicament for the inhibition of cell cycle progression.

Proteins, polypeptides and peptides can be introduced into the cells by various methods known in the art. For example, amphiphilic molecules may be membrane permeable and can enter cells directly. Membrane-bound proteins or polypeptides (usually lipophilic molecules or containing transmembrane domains) may insert directly into cell membranes and can thus exert their biological function. Other ways of introduction or intracellular uptake include microinjection, lipofection, receptor-mediated endocytosis, or the use of suitable carrier-molecules, particularly carrier-peptides. Suitable carrier-peptides include or can be derived from HIV-tat, antennapedia-related peptides (penetratins), galparan (transportan), polyarginine-containing peptides or polypeptides, Pep-1, herpes simplex virus VP-22 protein. Another possible introduction method is to introduce nucleic acid vectors capable of expressing such proteins, polypeptides or peptides Suitable methods to produce isolated polypeptides are known in the art. For example, such a method may comprise transferring the expression sector with an operably linked nucleic acid molecule encoding the polypeptide into a suitable host cell, cultivating said host cells under conditions which will permit the expression of said polypeptide or fragment thereof and, optionally, secretion of the expressed polypeptide into the culture medium. Depending on the cell-type different desired modifications, e.g. glycosylation, can be achieved.

The proteins, polypeptides and peptides may also be produced synthetically, e.g. by solid phase synthesis (Merrifield synthesis).

The polypeptides used in the invention may also include fusion polypeptides. In such fusion polypeptides another polypeptide may be fused at the N-terminus or the C-terminus of the polypeptide of interest or fragment thereof. A fusion polypeptide is produced by fusing a nucleic acid sequence (or a portion thereof) encoding another polypeptide to a nucleic acid sequence (or a portion thereof) of the present invention. Techniques for producing fusion polypeptides are known in the art and include ligating the coding sequences so that they are in frame and the expression of the fusion polypeptide is under control of the same promotor(s) and terminator.

Expression of the polypeptides of interest may also be performed using in vitro produced synthetic mRNA. Synthetic mRNA can be efficiently translated in various cell-free systems, including but not limited to, wheat germ extracts and reticulocyte extracts, as well as efficiently translated in cell based systems including, but not limited to, microinjection into frog oocytes, preferably *Xenopus laevis* oocytes.

Inhibition of cell cycle progression using said isolated proteins or polypeptides can be achieved by different ways familiar to the person skilled in the art: Overexpression of the protein or polypeptide may lead to suppression of the endogenous protein's biological function. By introducing deletions or other mutations, or by using suitable fragments, it is possible to generate sequences encoding dominant-negative peptides or polypeptides. Such dominant-negative peptides or polypeptides can inhibit the function of the corresponding endogenous protein. For example, fragments or mutants can be generated which consist only of binding domains but are enzymatically inactive (i.e. partially lacking their biological function). Such dominant-negative molecules may interfere with the biological function of the endogenous proteins or polypeptides by binding to intracellular binding partners and thus blocking activation of the endogenous molecule.

In another aspect, the invention relates to the use of an antibody which is directed against at least one polypeptide comprising a sequence as defined above for the manufacture of a medicament for the inhibition of cell cycle progression.

The term "antibody" as used herein includes both polyclonal and monoclonal antibodies, as well as fragments thereof, such as Fv, Fab and F(ab)$_2$ fragments that are capable of binding antigen or hapten. The present invention also contemplates "humanized" hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art.

Specifically, said antibodies or suitable fragments thereof, particularly in humanized form, may be used as therapeutic agents in a method for treating cancer and other proliferative diseases.

The use of said antibodies may also include the therapeutical inhibition of the above identified nucleic acid molecules or their corresponding polypeptides. In particular, this use may be directed to a proliferative disease.

The antibodies or fragments may be introduced into the body by any method known in the art. Delivery of antibodies, particularly of fragments, into live cells may be performed as described for peptides, polypeptides and proteins. If the antigen is extracellular or an extracellular domain, the antibody may exert its function by binding to this domain, without need for intracellular delivery.

Antibodies can be coupled covalently to a detectable label, such as a radiolabel, enzyme label, luminescent label, fluorescent label or the like, using linker technology established for this purpose. Labeling is particularly useful for diagnostic purposes (see below) or for monitoring the distribution of the antibody within the body or a neoplastic tumor, e.g. by computed tomography, PET (positron emission tomography), or SPECT (single photon emission computed tomography).

In another embodiment, the invention relates to the use of nucleic acid molecules, peptides, polypeptides, proteins, or antibodies, as defined above, for the manufacture of a medicament for the treatment or therapy of a proliferative disease.

In a preferred embodiment, the disease is coronary restenosis or a neoplastic disease, the latter preferably selected from the group consisting of lymphoma, lung cancer, colon cancer, ovarian cancer and breast cancer (see above).

"Proliferative diseases" according to the present invention are diseases associated with excessive cell division or proliferation as for example cancer. Preferably, the proliferative disease is restenosis, particularly coronary restenois, or a neoplastic disease, the latter preferably selected from the group consisting of lymphoma, lung cancer, colon cancer, ovarian cancer and breast cancer.

Restenosis is a re-narrowing of a blood vessel due to growth of tissue at the site of angioplasty or stent implantation. Stents are tiny metal tubes to hold the previously blocked arteries open. However, restenosis still develops in many patients with implanted stents, thus necessitating second angioplasty, stent implantation or even coronary bypass surgery.

Neoplastic diseases are diseases caused by newly forming tissue or cells. In the context of the present invention, the most relevant neoplastic diseases are neoplastic tumors, particularly selected from the group consisting of lymphoma, lung cancer, colon cancer, ovarian cancer and breast cancer.

In another aspect, the invention relates to the use of an isolated nucleic acid molecule comprising a nucleic acid with a sequence selected from the group of sequences consisting of:

a) the nucleic acid sequences presented in SEQ ID NO. 5, 7, 9, 11, 13, 1, 3;

b) nucleic acid sequences encoding polypeptides that exhibit a sequence identity with the protein encoded by a nucleic acid according to a) of at least 25% over 100 residues and/or which are detectable in a computer aided search using the BLAST sequence analysis programs with an e-value of at most $10^{-5}$, c) sequences of nucleic acid molecules which are capable of hybridizing with the nucleic acid molecules with sequences corresponding to (a) or (b) under conditions of medium or high stringency, d) the antisense-sequence of any of the sequences as defined in (a), (b) or (c), e) fragments of (a), (b), (c) or (d), f) RNA sequences corresponding to any of the sequences as defined in (a), (b), (c), (d), or (e), for the manufacture of a medicament for the activation of cell cycle progression.

In another aspect, the invention relates to the use of a an isolated peptide or polypeptide comprising a peptide or polypeptide with a sequence selected from the group consisting of:
(a) a sequence as disclosed in SEQ ID NO. 6, 8, 10, 12, 14, 2, 4;
(b) a sequence that exhibits a sequence identity with any of the sequences according to (a) of at least 25% over 100 residues.
(c) fragments of the sequences defined in (a) or (b), for the manufacture of a medicament for the activation of cell cycle progression.

In another aspect, the invention relates to the use of an antibody which is directed against at least one peptide or polypeptide with a sequence as defined above for the manufacture of a medicament for the activation of cell cycle progression.

Thus, another use or method involving the above identified nucleic acid sequences, peptides, polypeptides, proteins, and antibodies is directed towards the treatment of a disease in which cell cycle progression, is abnormal, deficient or negatively affected.

Diseases with abnormal, deficient or negatively affected cell cycle progression may be characterized by increased apoptosis and developmental disorders, in particular growth retardation, or slowed wound healing.

Therefore, a preferred embodiment of the present invention relates to a use or method of the treatment of a disease, wherein the disease is characterized by increased apoptosis, growth retardation, or slowed wound healing.

"Activation of cell cycle progression" includes both initiation and stimulation of cell cycle progression.

The use may include, but is not limited to, the use of said nucleic acid molecules and their corresponding polypeptides for direct or indirect activation of the expression of said target genes and/or for activation of the function of said target genes. In particular, the use may include the replacement for or the complementation of a lack of function or activity of an endogenous gene involved in cell cycle control or, particularly, in cell cycle progression.

Expression of RNA or polypeptides may be achieved by introduction of genomic DNA or cDNA containing suitable promoters, preferably constitutive or homologous promoters. Alternatively, any suitable nucleic acid expression vector can be used (see also above). The encoded protein or polypeptide may be full-length or a fragment or peptide with a similar biological function in cell cycle control or progression, particularly with the capability to activate cell cycle progression.

All gene therapy techniques known in the art can be used to introduce the sequences into cells or tissues of a subject suffering from a disease negatively affecting cell cycle progression. Particularly useful for introduction of the above identified sequences are viral vectors, e.g. retroviral or adenoviral vectors, lipofection and electroporation.

The proteins, polypeptides or peptides may also be generated by any known in vivo or in vitro method and introduced directly into the cells (see above).

It is known that suitable antibodies can be used to activate the biological function of target proteins they bind to. Activation may occur by inducing conformational changes upon binding to the target protein. Another possibility is that the antibody binds two or more target proteins and brings them into sufficiently close physical proximity to induce interaction of the target proteins. The latter mode of activation is particularly known for membrane-bound dimeric receptors.

With respect to the specific embodiments relating to the used nucleic acids, peptides, polypeptides, proteins, and antibodies the same applies as defined above for the other uses of the invention.

In another embodiment, the invention relates to a medicament containing an isolated nucleic acid molecule, peptide, polypeptide, or antibody selected from the group consisting of
a) nucleic acid molecules or nucleic acid expression vectors as defined above,
b) a peptide or polypeptide comprising a sequence as defined above,
c) an antibody directed against at least one peptide or polypeptide according to (b).

Preferably this isolated nucleic acid molecule is an RNA molecule and preferably is double-stranded. Particularly the isolated nucleic acid molecule is an siRNA molecule according to the present invention.

The medicaments may be used or applied in methods for the therapy of any kind of proliferative disease, such as cancer, preferably for the therapy of diseases in which cell cycle control or cell cycle progression play a role, particularly for the therapy of a lymphoma, lung cancer, colon cancer, ovarian cancer or breast cancer.

The medicaments may also be used or applied in methods for the therapy of any kind of disease associated with abnormal or deficient cell cycle progression, particularly diseases characterized by increased apoptosis, developmental disorders or abnormalities (particularly growth retardation) and slowed wound healing.

The following considerations for medicaments and their administration apply also to the medicaments of the invention as to the above disclosed uses.

The medicament preferably comprises additionally a suitable pharmaceutically acceptable carrier, preferably virus-particles or virus-derived particles that may harbour the viral vectors, transfection solutions comprising liposomes, particularly cationic liposomes, calcium phosphate etc. Preferably a carrier is used, which is capable of increasing the efficacy of the expression vector or virus particles containing the expression vector to enter the mammalian target cells. The medicament may additionally comprise other carrier substances, preferably starch, lactose, fats, stearin acid, alcohol, physiological NaCl-solutions or further additives, in particular stabilizers, preservatives, dyes and flavourings.

The medicaments may also comprise other suitable substances. For example, RNA or siRNA containing medicaments may contain substances which stabilize double-stranded RNA molecule and/or which enable the double-stranded RNA molecule or DNA expression vector to be transfected or to be injected into the human or animal cell.

Administration can be carried out by known methods, wherein a nucleic acid is introduced into a desired cell in vitro or in vivo. For therapeutic applications, the medicament may be in form of a solution, in particular an injectable solution, a cream, ointment, tablet, suspension, granulate or the like. The medicament may be administered in any suitable way, in particular by injection, by oral, nasal, rectal application. The medicament may particularly be administered parenteral, that means without entering the digestion apparatus, for example by subcutaneous injection. The medicament may also be injected intravenously in the form of solutions for infusions or injections. Other suitable administration forms may be direct administrations on the skin in the form of creams, ointments, sprays and other transdermal therapeutic substances or in the form of inhalative substances, such as nose sprays, aerosoles or in the form of microcapsules or implantates.

The optimal administration form and/or administration dosis for a medicament either comprising double-stranded RNA molecules with the above sequences or comprising nucleic acid vectors capable to express such double-stranded RNA molecules depend on the type and the progression of the disease to be treated.

Preferably, the activator or inhibitor is administered in pharmaceutically effective amount. As used herein, a "pharmaceutically effective amount" of an activator or inhibitor is an amount effective to achieve the desired physiological result, either in cells treated in vitro or in a subject treated in vivo. Specifically, a pharmaceutically effective amount is an amount sufficient to positively influence, for some period of time, one or more clinically defined pathological effects associated with a proliferative disease or a disease associated with abnormal, deficient or negatively affected cell cycle progression. The pharmaceutically effective amount may vary depending on the specific activator or inhibitor selected, and is also dependent on a variety of factors and conditions related to the subject to be treated and the severity of the disease. For example, if the activator or inhibitor is to be ministered in vivo, factors such as age, weight, sex, and general health of the patient as well as dose response curves and toxicity data obtained in pre-clinical animal tests would be among the factors to be considered. If the activator or inhibitor is to be contacted with cells in vitro, one would also design a variety of pre-clinical in vitro studies to asses parameters like uptake, half-life, dose, toxicity etc. The determination of a pharmaceutically effective amount for a given agent (activator or inhibitor) is well within the ability of those skilled in the art Preferably, the activator or inhibitor is present in a concentration of 0.1 to 50% per weight of the pharmaceutical composition, more preferably 10 to 30%.

An inhibitor, activator, or drug according to the present invention may also be a "small molecule". Small molecules are molecules which are not proteins, peptides antibodies or nucleic acids, and which exhibit a molecular weight of less than 5000 Da, preferably less than 2000 Da, more preferably less than 2000 Da, most preferably less than 500 Da. Such small molecules may be identified in high throughput procedures/screening assays starting from libraries. Such methods are known in the art. Suitable small molecules can also be designed or further modified by methods known as combinatorial chemistry.

The genes/proteins that are provided by the current application and that possess one of the sequences as defined in (a) to (f), can be used in a high-throughput or other screen for new agents that inhibit or activate cell cycle progression. Particularly inhibitors of cell cycle progression identified by such a screen may be used as medicaments for the therapy of proliferative diseases, particularly for the therapy of a disease in which cell cycle control or cell cycle progression play a role.

In another aspect, the present invention relates to the use of an isolated nucleic acid molecule comprising a sequence as defined above or the use of a ligand binding specifically at least one polypeptide comprising a sequence as defined above for the in vitro diagnosis of a proliferative disease or a disease associated with abnormal cell cycle progression.

In a preferred embodiment, diagnosis relates to proliferative diseases as defined above.

In another preferred embodiment, diagnosis relates to diseases associated with abnormal, deficient or negatively affected cell cycle progression, as they are described above. Diseases with "abnormal" cell cycle progression include diseases in which cell cycle progression is deficient or negatively affected.

In a proliferative disease, expression of endogenous genes corresponding to the above identified sequences may be increased.

In a disease in which cell cycle progression is abnormal, deficient or negatively affected, expression of the corresponding endogenous genes may be lowered. Furthermore, the corresponding endogenous gene may be mutated, rendering the corresponding protein less active or non-functional.

The diagnostic use of the above identified nucleic acid molecules and probes may include, but is not limited to the quantitative detection of expression of said target genes in biological probes (preferably, but not limited to tissue samples, cell extracts, body fluids, etc.), particularly by quantitative hybridization to the endogenous nucleic acid molecules comprising the above-characterized nucleic acid sequences (particularly cDNA, RNA)

Expression of the endogenous genes or their corresponding proteins can be analyzed in vitro in tissue samples, body fluids, and tissue and cell extracts. Expression analyis can be performed by any method known in the art, such as RNA in situ hybridization, PCR (including quantitative RT-PCR), and various serological or immunological assays which include, but are not limited to, precipitation, passive agglutination, enzyme-linked immunosorbent antibody (ELISA) technique and radioinmunoassay techniques.

The diagnostic use may also include the detection of mutations in endogenous genes corresponding to the above identified nucleic acid sequences.

Suitable nucleic acid probes may be synthesized by use of DNA synthesizers according to standard procedures or, preferably for long sequences, by use of PCR technology with a selected template sequence and selected primers. The probes may be labeled with any suitable label known to those skilled in the art, including radioactive and non-radioactive labels. Typical radioactive labels include $^{32}P$, $^{125}I$, $^{35}S$, or the like. A probe labeled with a radioactive isotope can be constructed from a DNA template by a conventional nick translation reaction using a DNase and DNA polymerase. Non-radioactive labels include, for example, ligands such as biotin or thyroxin, or various luminescent or fluorescent compounds. The probe may also be labeled at both ends with different types of labels, for example with an isotopic label at one end and a biotin label at the other end. The labeled probe and sample can then be combined in a hybridization buffer solution and held at an appropriate temperature until annealing occurs. Such nucleic acid probes may also be used for other than diagnostic purposes, e.g. for the identification of further homologs or orthologs.

"Ligands" binding specifically to said polypeptides are known in the art Such ligands include proteins or polypeptides, for example intracellular binding partners, antibodies, molecular affinity bodies, and small molecules. Specifically binding ligands can be identified by standard screening assays known in the art (see also below), for example by yeast two-hybrid screens and affinity chromatography. A specifically binding ligand does not need to exert another function such as inhibiting or activating the molecule with which it interacts.

In a preferred embodiment, the ligand is an antibody binding specifically at least one polypeptide comprising a sequence as defined above.

"Specific binding" according to the present invention means that the polypeptide to be identified (the target polypeptide) is bound with higher affinity than any other polypeptides present in the sample. Preferred is at least 3 times higher affinity, more preferred at least 10 times higher affinity, and most preferred at least 50 times higher affinity.

Non-specific binding ("cross-reactivity") may be tolerable if the target polypeptide can be identified unequivocally, e.g. by its size on a Western blot Preferably the specifically binding ligands can be labeled, e.g. with fluorescent labels, enzymes, molecular tags (e.g. GST, myc-tag or the like), radioactive isotopes, or with labeled substances, e.g. labeled secondary antibodies. For MRI (magnetic resonance imaging), the ligands may be chelated with gadolinium, superparamagnetic iron oxide or lanthanides. For PET (positron emission tomography) or SPECT (single photon emission computed tomography) commonly used isotopes include $^{11}C$, $^{18}F$, $^{15}O$, $^{13}N$, $^{86}Y$, $^{90}Y$, and $^{16}Co$.

In another aspect, the present invention relates to a diagnostic kit containing an isolated nucleic acid molecule as defined above and/or a ligand which is directed against at least one polypeptide as defined above for the in vitro diagnosis of a proliferative disease or a disease associated with abnormal cell cycle progression.

Diagnostic kits may comprise suitable isolated nucleic acid or amino acid sequences of the above identified genes or gene products, labelled or unlabelled, and/or specifically binding ligands (e.g. antibodies) thereto and auxiliary reagents as appropriate and known in the art. The assays may be liquid phase assays as well as solid phase assays (i.e. with one or more reagents immobilized on a support). The diagnostic kits may also include ligands directed towards other molecules indicative of the disease to be diagnosed.

In another aspect, the invention relates to the use of an isolated nucleic acid molecule or a nucleic acid expression vectors as defined above or of an antibody which is directed against at least one polypeptide comprising a sequence as defined above, in a screening assay for the identification and characterization of drugs that inhibit or activate cell cycle progression.

In another aspect, the invention relates to the use of a peptide, polypeptide or protein with a sequence as defined above in a screening assay for interacting drugs, that inhibit or activate cell cycle progression. Such interacting molecules may also be used as ligands for diagnosis as described above.

"Screening assay" according to the present invention relates to assays which allow to identify substances, particularly potential drugs, that inhibit or activate cell cycle progression by screening libraries of substances. "Screening assay" according to the present invention also relates to assays to screen libraries for substances capable of binding to the nucleic acids, polypeptides, peptides or antibodies defined above. Suitable libraries may, for example, include small molecules, peptides, polypeptides or antibodies.

The invention relates to assays for identification as well as to assays for characterization of substances that inhibit or activate cell cycle progression or bind to said nucleic acids, polypeptides, peptides or antibodies. Particularly, the invention relates to screening assays for drugs. Such drugs may be identified and characterized from libraries of unspecified compounds as well as libraries of drugs which are already known for treatment of other diseases. For such known drugs also potential side-effects and therapeutically applicable doses are known.

Suitable drugs include "interacting drugs", i.e. drugs that bind to the polypeptides or nucleic acids identified above. Such interacting drugs may either inhibit or activate the molecule they are bound to. Examples for interacting substances are peptide nucleic acids comprising sequences identified above, antisense RNAs, siRNAs, ribozymes, aptamers, antibodies and molecular affinity bodies (CatchMabs, Netherlands). Such drugs may be used according to any aspect of the present invention, including use for the manufacture of medicaments and methods of treatment of proliferative diseases. It is known that such interacting drugs can also be labeled and used as ligands for diagnosis of a disease associated with cell cycle control or cell cycle progression.

Suitable screening assays are known in the art For example, in a preferred embodiment of the invention the screening method for the identification and characterization of an inhibitor or an activator molecule that inhibits or activates cell cycle progression comprises the following steps:
a) transformation of a nucleic acid molecule or a nucleic acid expression vector as defined above into a host cell or host organism,
b) cultivation of the host cell or host organism obtained in step a) under conditions that allow the overexpression of the polypeptide or RNA encoded by or corresponding to the nucleic acid of step (a) either in the presence or in the absence of at least one candidate for an inhibitor- or activator-molecule, and
c) analysis of the cell cycle progression in the cultivated cell or organism and thereby identification of an inhibitor or activator of cell cycle progression.

The term "expression vector" as used herein does not only relate to RNA or siRNA expressing vectors, but also to vectors expressing peptides, polypeptides or proteins.

The transfer of the expression vector into the host cell or host organism hereby may be performed by all known transformation or transfection techniques, including, but not limited to calcium phosphate transformation, lipofection, microinjection. Host cell/host organisms may be all suitable cells or organisms that allow detection of impaired cell division, preferably of impaired cell cycle control or cell cycle progression. A particularly preferred host organism is *C. elegans,* since its translucent body allows an easy detection of failures during cell division, including cell cycle progression. Vertebrate cells, preferably mammalian, more preferably human cells, in particular human cell lines are also preferred host cells. The expression vector may be any known vector that is suitable to allow the expression of the nucleic acid sequence as defined above. Preferred expression vectors possess expression cassettes comprising a promoter that allows an overexpression of the RNA, peptide or polypeptide as defined above.

After the transfer of the expression vector into the host cell/host organism one part of the host cells or host organisms are cultured in the presence of at least one candidate of an inhibitor- or activator-molecule and under culture conditions that allow the expression, preferably the overexpression of the RNA, peptide or polypeptide as defined above. The other part of the transfected host cells are cultured under the same culture conditions, but in the absence of the candidate of an inhibitor- or activator-molecule.

Finally, after an appropriate incubation time/culture period the proliferation state and/or cell divisions for host cells or host organisms that had been cultured in the presence or in the absence of the at least one candidate for an inhibitor or an activator molecule are detected or preferably quantified. This detection or quantification step is preferably done by time lapse fluorescence or DIC microscopy, particularly in those cases when the host organism is *C. elegans* or another mostly translucent organism that is available to be analysed by time lapse fluorescence or DIC microscopy. The detection /quantification step may also be done by any other technique known to the state of the art that is suitable to analyse the proliferation state or the extent of cell division, preferably all kinds of microscopic techniques.

In another preferred embodiment, the screening method for the identification and characterization of an interacting molecule that inhibits or activates cell cycle progression from a library of test substances comprises the following steps:

a) recombinantly expressing a polypeptide encoded by a nucleic acid molecule sequence as defined above in a host cell, b) isolating and optionally purifying the recombinantly expressed polypeptide of step (a), c) optionally labelling of the test substances and/or labelling of the recombinantly expressed polypeptide, d) immobilizing the recombinantly expressed polypeptide to a solid phase, e) contacting of at least one test substance with the immobilized polypeptide, f) optionally one or more washing steps, g) detecting the binding of the at least one test substance to the immobilized polypeptide at the solid phase, and h) performing a functional assay for inhibition or activation of cell cycle progression.

Step a) includes the recombinant expression of the above identified polypeptide or of its derivative from a suitable expression system, in particular from cell-free translation, bacterial expression, or baculuvirus-based expression in insect cells.

Step b) comprises the isolation and optionally the subsequent purification of said recombinantly expressed polypeptides with appropriate biochemical techniques that are familiar to a person skilled in the art.

Alternatively, these screening assays may also include the expression of derivatives of the above identified polypeptides which comprises the expression of said polypeptides as a fusion protein or as a modified protein, in particular as a protein bearing a "tag"-sequence. These "tag"-sequences consist of 'short nucleotide sequences that are ligated 'in frame' either to the N- or to the C-terminal end of the coding region of said target gene. Commonly used tags to label recombinantly expressed genes are the poly-Histidine-tag which encodes a homopolypeptide consisting merely of histidines, particularly six or more histidines, GST (glutathion S-transferase), c-myc, FLAG®, MBP (maltose binding protein), and GFP. In this context the term "polypeptide" does not merely comprise polypeptides with the nucleic acid sequences of SEQ ID No. 1 to 31, their naturally occurring homologs, preferably orthologs, more preferably human orthologs, but also derivatives of these polypeptides, in particular fusion proteins or polypeptides comprising a tag-sequence.

These polypeptides, particularly those labelled by an appropriate tag-sequence (for instance a His-tag or GST-tag), may be purified by standard affinity chromatography protocols, in particular by using chromatography resins linked to anti-His-tag-antibodies or to anti-GST-antibodies which are both commercially available. Alternatively, His-tagged molecules may be purified by metal chelate affinity chromatography using Ni-ions. Alternatively to the use of 'label-specific' antibodies the purification may also involve the use of antibodies against said polypeptides. Screening assays that involve a purification step of the recombinantly expressed target genes as described above (step 2) are preferred embodiments of this aspect of the invention.

In an—optional—step c) the compounds tested for interaction may be labelled by incorporation of radioactive isotopes or by reaction with luminescent or fluorescent compounds. Alternatively or additionally also the recombinantly expressed polypeptide may be labelled.

In step d) the recombinantly expressed polypeptide is immobilized to a solid phase, particularly (but not limited) to a chromatography resin. The coupling to the solid phase is thereby preferably established by the generation of covalent bonds.

In step e) a candidate chemical compound that might be a potential interaction partner of the said recombinant polypeptide or a complex variety thereof (particularly a drug library) is brought into contact with the immobilized polypeptide.

In an—optional—step f) one or several washing steps may be performed. As a result just compounds that strongly interact with the immobilized polypeptide remain bound to the solid (immobilized) phase.

In step g) the interaction between the polypeptide and the specific compound is detected, in particular by monitoring the amount of label remaining associated with the solid phase over background levels.

Such interacting molecules may be used without functional characterization for diagnostic purposes as described above.

In step h) the interacting molecule is further analyzed for inhibition or activation of cell cycle progression. Such analysis or functional assay can be performed according to any assay system known in the art A suitable assay may include the cultivation of a host cell or host organism in the presence (test condition) or absence (control condition) of the interacting molecule, and comparison of cell cycle progression under test and control conditions.

In another aspect, the invention relates to a method for the preparation of a pharmaceutical composition wherein an inhibitor or activator of cell cycle progression is identified according to any of the screening methods described above, synthesized in adequate amounts and formulated into a pharmaceutical composition.

Suitable methods to synthesize the inhibitor or activator molecules are known in the art. For example, peptides or polypeptides can be synthesized by recombinant expression (see also above), antibodies can be obtained from hybridoma cell lines or immunized animals. Small molecules can be synthesized according to any known organic synthesis methods.

Adequate amounts relate to pharmaceutically effective amounts.

Similarly, said inhibitor or activator may be provided by any of the screening methods described above and formulated into a pharmaceutical composition.

BRIEF DESCRIPTION OF THE DRAWINGS

FIG. 1 shows DIC microscopy images taken from time-lapse recording of the first round of cell division in *C. elegans* F1 progeny from an F0 parent treated with dsRNA (RNAi) directed against F59E12.11.

FIG. 2 shows an amino acid sequence alignment of F59E12.11 (SEQ ID NO. 2) and the corresponding human ortholog NP_477517 (SEQ ID NO. 4).

FIG. 4 shows an amino acid sequence alignment of Y71H2B.3 (SEQ ID NO. 6) and its corresponding human and *Drosophila* orthologs: NP_001542 (SEQ ID NO. 8), AAD05364 (SEQ ID NO. 10), AAF53289 (SEQ ID NO. 12) and NP_013741 (SEQ ID NO. 14).

FIG. 5 shows DIC microscopy images taken from time-lapse recording of the first two rounds of cell division in wild type untreated *C. elegans*.

mRNA, remaining mRNA levels (% of negative control treated sample); pos. ctrl., positive control; neg. ctrl., negative control

Figure 3:
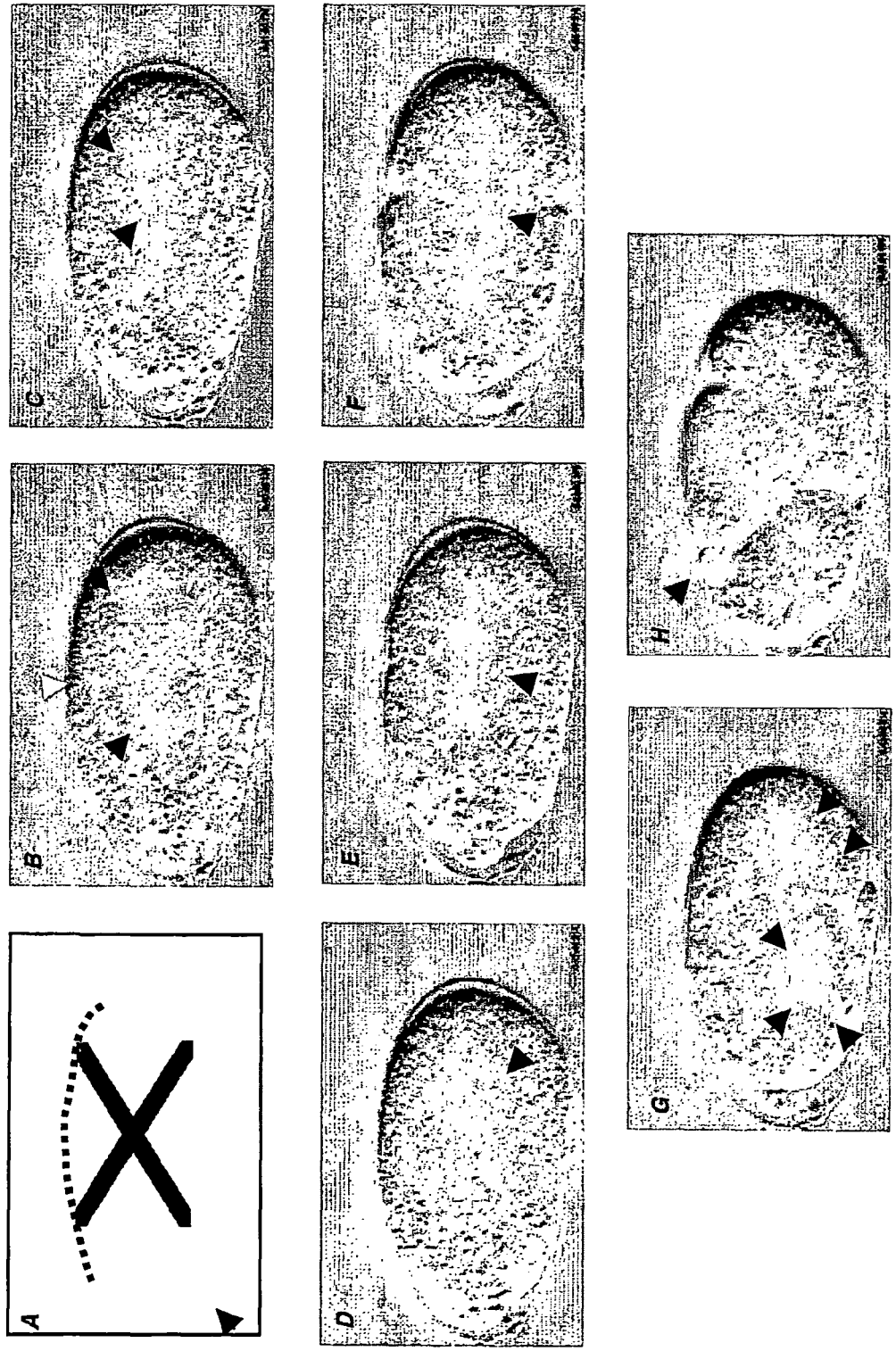
FIG. 3 shows DIC microscopy images taken from time-lapse recording of the first two rounds of cell division in *C. elegans* F1 progeny from F0 a parent treated with dsRNA (RNAi) directed against Y71H2B.3.
Figure 6:
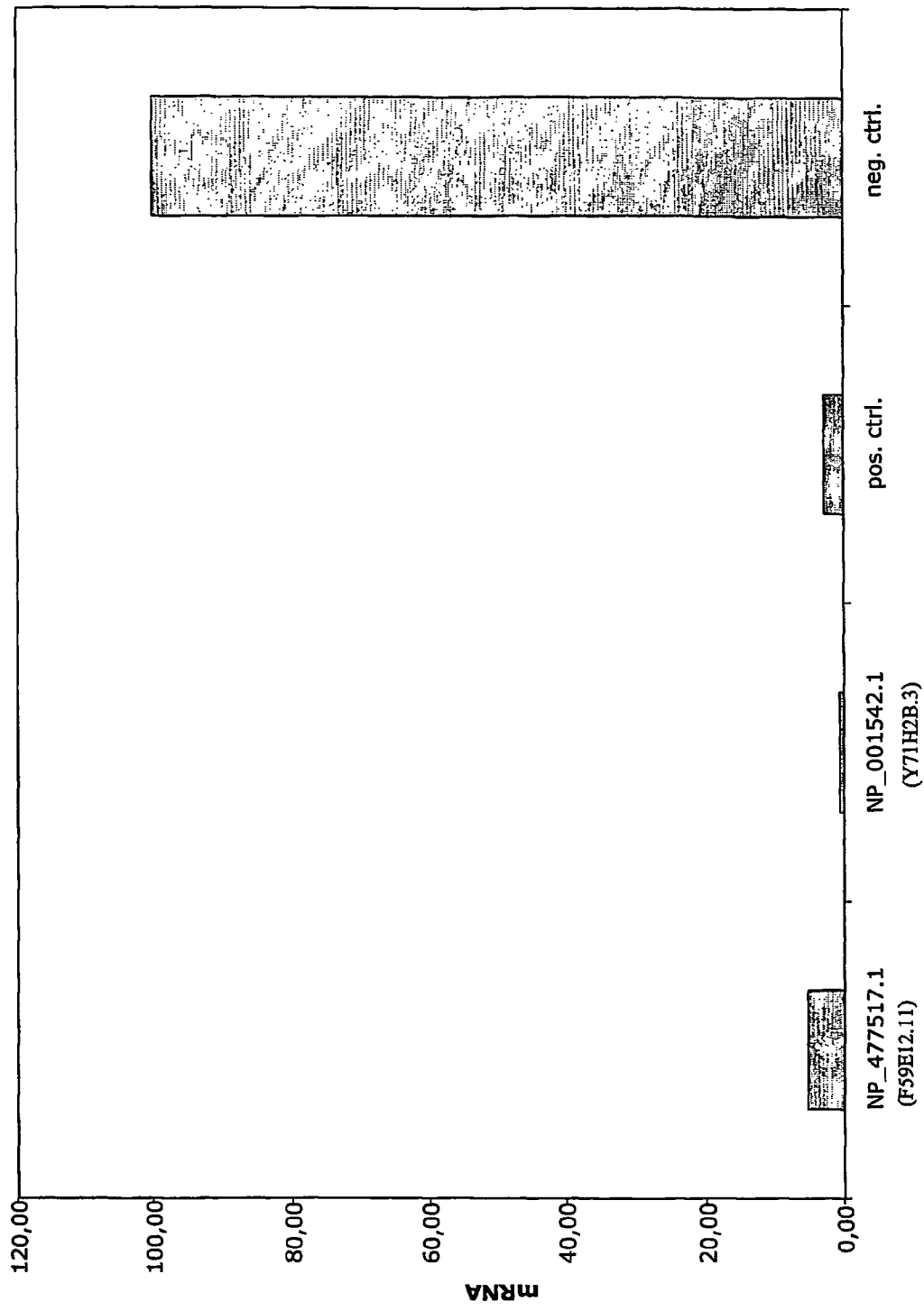
FIG. 6: shows the remaining mRNA levels after RNAi treatment of HeLa cells. RNAi treatment of HeLa cells with siRNAs directed against NP_477517.1 and NP_001542.1, the human orthologs of *C. elegans* genes F59E12.11 and Y71H2B.3, respectively, results in the specific reduction to mRNA levels below 10% compared control treated samples.
Figure 7:
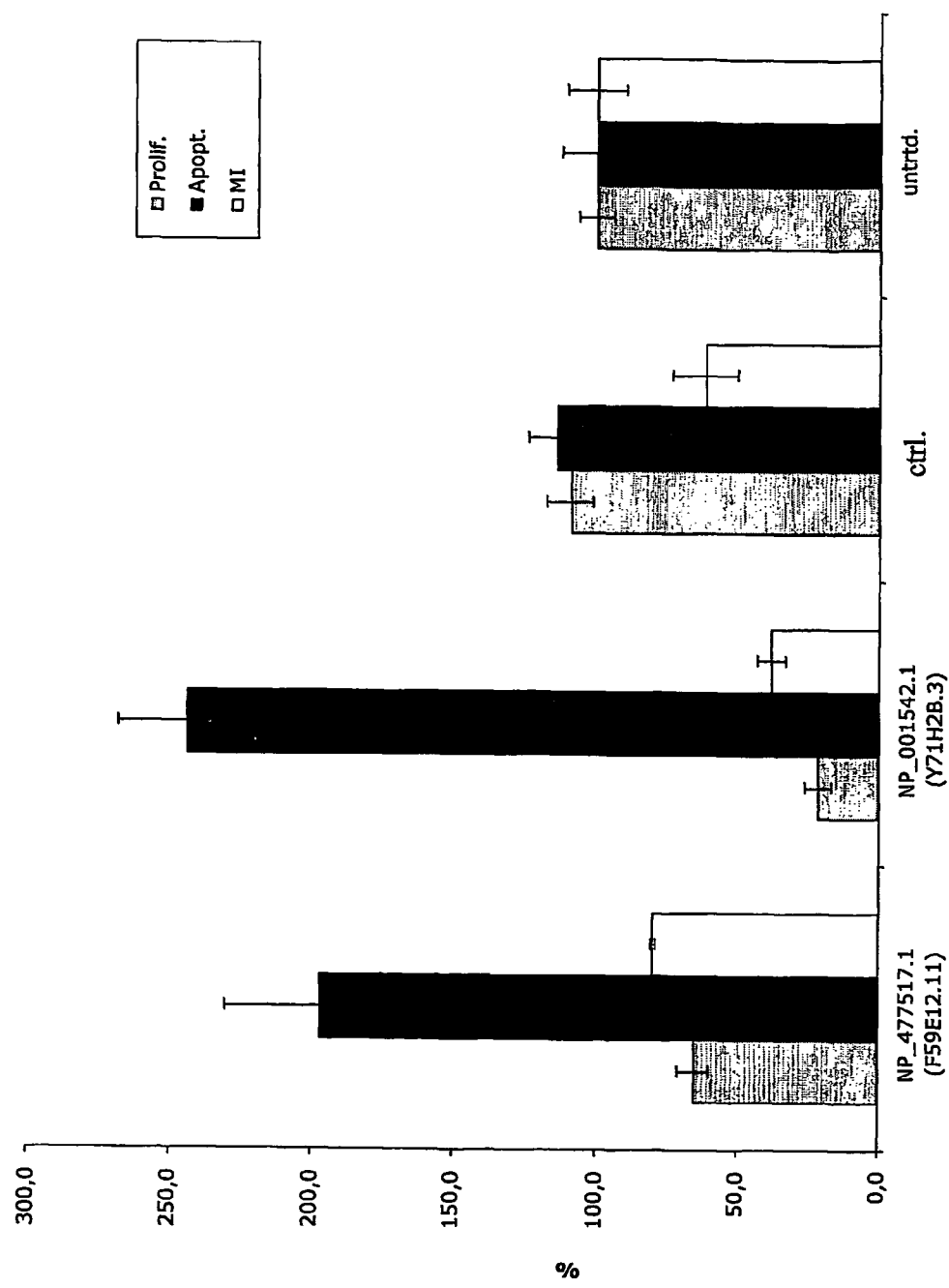
FIG. 7: shows the effect of RNAi treatment on cell proliferation, apoptosis, and mitosis in HeLa cells. For graphical presentation, proliferation, apoptosis rate, and MI of untreated cells were set to 100.

prolif., cell proliferation; apopt., apoptosis; MI; mitotic index; %, percent of untreated sample; scr. ctrl., scrambled control; untrtd., untreated.

The following examples illustrate the present invention without, however, limiting the same thereto.

EXAMPLE 1

Protocol for Identifying Functional Orthologs in Other Species

To identify orthologous genes, the following procedure was used: The identified homologous amino acid sequences themselves were used for BLAST searches. If the original *C. elegans* protein was (re-)identified by a BLAST hit with an e-value of less than $10^{-5}$, the identified homolog was defined as an ortholog. The BLAST search was performed with the default parameters and the low complexity filter on. An alternative parameter for identification of homologous genes can be the percentage of sequence identity. Over 100 residues, a sequence identity of 30% defines a homologous gene. After the BLAST search is completed, multiple sequence alignment is performed using appropriate software (for example, CLUSTALW) and a neighbour joining phylogenetic tree is generated. Any person skilled in the art can identify the human ortholog from a phylogenetic tree. Essentially, the human sequence that is separated on the tree by a single speciation event or most closely related on the tree is likely to be an ortholog.

EXAMPLE 2

Generation of dsRNA Molecules for RNAi Experiments

First, oligonucleotide primer pair sequences were selected to amplify portions of the gene of interest's coding region using standard PCR techniques. Primer pairs were chosen to yield PCR products containing at least 500 bases of coding sequence, or a maximum of coding bases for genes smaller than 500 bases. In order to permit the subsequent use of the PCR product as a template for in vitro RNA transcription reactions from both DNA strands, the T7 polymerase promoter sequence "TAATACGACTCACTATAGG" (SEQ ID NO. 15) was added to the 5' end of forward primers, and the T3 polymerase promoter sequence "AATTAACCCTCACTAAAGG" (SEQ ID NO. 16) was added to the 5' end of reverse primers. The synthesis of oligonucleotide primers was completed by a commercial supplier (Sigma-Genosys, UK or MWG-Biotech, Germany).

PCR reactions were performed in a volume of 50 µl, with Taq polymerase using 0.8 µM primers and approximately 0.1 µg of wild-type (N2 strain) genomic DNA template. The PCR products were EtOH precipitated, washed with 70% ETOH and resuspended in 7.0 µl TE. 1.0 µl of the PCR reaction was pipetted into each of two fresh tubes for 5 µl transcription reactions using T3 and T7 RNA polymerases. The separate T3 and T7 transcription reactions were performed according to the manufacturer's instructions (Ambion, Megascript kit), each diluted to 50 µl with RNase-free water and then combined. The mixed RNA was purified using RNeasy kits according to the manufacturer's instructions (Qiagen), and eluted into a total of 130 µl of RNase-free $H_2O$. 50 µl of this was mixed with 10 µl 6× injection buffer (40 mM $KPO_4$ pH 7.5, 6 mM potassium citrate, pH 7.5, 4% PEG 6000). The RNA was annealed by heating at 68° C. for 10 min, and at 37° C. for 30 min. Concentration of the final dsRNAs were measured to be in the range of 0.1-0.3 µg/µl. The products of the PCR reaction, of the T3 and T7 transcription reactions, as well as the dsRNA species were run on 1% agarose gels to be examined for quality control purposes. Success of double stranding was assessed by scoring shift in gel mobility with respect to single stranded RNA, when run on non-denaturing gels.

EXAMPLE 3

Injections of dsRNA and Phenotypic Assays dsRNAs were injected bilaterally into the syncytial portion of both gonads of wild-type (N2 strain) young adult hermaphrodites, and the animals incubated at 20° C. for 24 hrs. Embryos were then dissected out from the injected animals and analyzed by time-lapse differential interference contrast videomicroscopy for potential defects in cell division processes, capturing 1 image every 5 seconds, as previously described (Gönczy et al., Dissection of cell division processes in the one cell stage *Caenorhabditis elegans* embryo by mutational analysis. *J Cell Biol* 144, 927-946 (1999)). For each experiment, embryos from at least 3 different injected worms were filmed in this manner, from shortly after fertilization until the four cell stage. Embryos from 2 additional injected worms were recorded for shorter periods, covering the 2 cell and the 4 cell stage, respectively, thus yielding documentation for at least 5 injected worms in each experiment.

In some cases, embryos exhibited acute sensitivity to osmotic changes, as evidenced by their loss of structural integrity during the dissection of the injected animals. In order to overcome this limitation, injected animals were not dissected, but rather, anaesthetized for 10 min in M9 medium containing 0.1% tricaine and 0.01% tetramisole, and mounted intact on an agarose pad to observe the F1 embryogenesis in utero (Kirby et al., Dev. Biol. 142, 203-215 (1990)). The resolution achieved by viewing through the body wall does not equal that achieved by observing dissected embryos, and only limited phenotypic analysis was conducted in these cases.

Three injected worms were also transferred to 3 fresh plates 24 hrs after injection of the dsRNA, and left at 18° C. Three days later, the plates were checked with a stereomicroscope (20-40× total magnification) for the presence of F1 larvae (L2's-L4's), as well as their developmental stage. Three days after that, the plates were inspected again for the presence of F1 adults, as well as their overall body morphology and the presence of F2 progeny.

EXAMPLE 4

Characterization of the *C. elegans* Gene F59E12.11 dsRNA was designed and used to specifically silence the expression of the *C. elegans* gene by RNAi, thereby testing its functional involvement in the first round of embryonic cell division in this metazoan species. The dsRNA was synthesized in vitro from PCR-amplified wild type genomic DNA fragments of the F59E12.11 gene. For PCR, the following primer pair was used: "TAATACGACTCACTATAGGG-GATTTCTTCAATCGGCTCA" (SEQ ID NO. 17) with "AATTAACCCTCACTAAAGGTATGTCGT-TCGTCCCATCAG" (SEQ ID NO. 18) as forward and reverse primers, respectively. The dsRNA was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilisation, while the female pronucleus is completing its meiotic divisions, until ~15 to 20 minutes later.

Control worms were either not injected, or injected with irrelevant dsRNA. Irrelevant dsRNA was made of the same nucleotide composition as the experimental dsRNA, but the nucleotides were in random order. In the F1 progeny of such control worms the cellular events of the first two rounds of embryonic cell division were found to exhibit very limited variability, as observed by DIC microscopy. All processes that were examined and scored for the possibility of phenotypic deviations are listed and illustrated in FIG. 5. Briefly, the antero-posterior polarity of the embryo is initially determined by the position of the male pronucleus at the cortex, shortly after entry into the egg. This is accompanied by a clear, coordinated flow of yolk granules through the central portion of the cytoplasm along the embryo's longitudinal axis towards the male pronucleus, and a concomitant series of cortical waves or ruffles progressing towards the anterior of the embryo. Shortly thereafter, the male and female pronuclei undergo highly patterned migrations resulting in their meeting within the posterior half of the embryo, followed by a centration and rotation of the pronuclear pair and associated centrosomes to set up the future mitotic spindle along the embryo's longitudinal axis. After synchronous breakdown of the pronuclear envelopes, the clearly bipolar mitotic spindle is initially short, but then rockingly elongates. These movements are accompanied by a slight posterior displacement of the posterior spindle pole, while the anterior spindle pole remains approximately stationary. This then results in an asymmetric positioning of the spindle during anaphase and telophase, thereby yielding an asymmetric placement of the cytokinetic furrow, and generating unequally-sized daughter cells: a smaller posterior P1 blastomere, and larger anterior AB blastomere. While the AB nucleus then migrates directly to the center of the AB cell, the P1 nucleus typically migrates further towards the posterior of that cell, before undergoing a pronounced 90° rotation while re-migrating to the anterior P1 cortex with one of its duplicated centrosomes leading. This insures that the P1 blastomere then divides along the embryo's longitudinal axis, perpendicular to that of the AB blastomere. These two divisions occur asynchronously, with P1 lagging 2-3 minutes behind AB.

In the F1 embryos of worms injected with dsRNA, the following highly reproducible phenotypes are observed (FIG. 1). The embryos show an irregular cytoplasmic texture. At the poles, areas of uncondensed chromosomal material can be observed (arrows). The embryos arrest development before pronuclear formation The phenotype is accompanied by osmotic instability, which presented itself by the embryo filling the egg shell. The phenotype is embryonic lethal.

All observed phenotypes indicate a requirement for F59E12.11 gene function in cell cycle progression during mitosis. Since this function is essential to cell division throughout metazoans, this gene and any homologs and derivatives thereof represent excellent tools for use in the development of a wide range of therapeutics including anti-proliferative agents. Analysis of the F59E12.11 gene sequence reveals a clear ortholog in human (GenBank Accession No. NP_477517), the sequence similarity being in the N-terminal half of the protein. The ortholog had no function ascribed to it until now. There has been no information linking the genes to cell cycle control or cell cycle progression. Based on the extremely high sequence conservation at the protein level, it can be concluded that the ortholog most likely encodes a protein with equivalent function in cell cycle progression in humans.

EXAMPLE 5

Characterization of the *C. elegans* Gene Y71H2B.3 dsRNA was designed and used to specifically silence the expression of the *C. elegans* gene by RNAi, thereby testing its functional involvement in the first 2 rounds of embryonic cell division in this metazoan species. The dsRNA was synthesized in vitro from PCR-amplified wild type genomic DNA fragments of Y71H2B.3. For PCR, the following primer pair was used: "TAATACGACTCACTATAGGTGCGAAAC-CTGAATTTTTCC" (SEQ ID NO. 19) with "AATTAAC-CCTCACTAAAGGGCTCATCAATTGAAACGGCT" (SEQ ID NO. 20) as forward and reverse primers, respectively. The dsRNA was purified, and injected into adult hermaphrodite worms. The phenotypic consequences of the RNAi treatment were documented 24 hours later in the F1 progeny of injected worms, using time-lapse differential interference contrast (DIC) microscopy. Embryo recordings started ~20 minutes after fertilisation, while the female pronucleus is completing its meiotic divisions, until the 4 cell stage, ~30 minutes later.

In the F1 progeny of control worms that were either not injected, or injected with irrelevant dsRNA, the cellular events of the first two rounds of embryonic cell division were found to exhibit very limited variability, as observed by DIC microscopy and described in Example 3.

In the F1 embryos of worms injected with dsRNA, the following highly reproducible phenotypes are observed (FIG. 3). There is a lack of cortical ruffling (symbolized by the cross in FIG. 3A) with some irregular blebbing at the anterior end of the embryo, resulting in attenuated furrowing at the pseudo-cleavage stage (FIG. 3B, white arrow). Pronuclei are small and irregular in shape (FIGS. 3B and C, black arrows). Pronuclei meet but are not centred, the mitotic spindle is set up at the posterior end of the embryo. The spindle is short, poorly visible and lacks spindle rocking (FIG. 3E), resulting in chromosome segregation defects (FIGS. 3F and G). At the two-cell stage irregular cortical blebbing was observed (FIG. 3G, arrows). The P1 cell divides significantly later than normal (FIG. 3H, arrow).

All observed phenotypes indicate a requirement for Y71H2B.3 gene function in gene function in cell cycle progression during cell division Since this function is essential to cell division throughout metazoans, this gene and any homologs and derivatives thereof represent excellent tools for use in the development of a wide range of therapeutics including anti-proliferative agents. Analysis of the Y71H2B.3 gene sequence has revealed orthologs in human (GenBank Accession No. NP_001542), rat (GenBank Accession No. AAD05364 or NP_113812), *Drosophila* (GenBank Accession No. AAF53289), and *Saccharomyces cerevisiae* (GenBank Accession No. NP_013741). The identified ortholog is immunoglobulin-binding protein 1, which is involved in IgRmediated signal transduction in B-cells. There has been no information regarding Y71H2B.3 or these orthologs having a role in cell cycle progression or cell division.

EXAMPLE 6

Effects of RNA; Treatment in Human Cells

Design and Synthesis of siRNAs

For all experiments in human cells short double stranded interfering RNAs (siRNAs) of 21 bases in length, comprised of a 19 bp core of complementary sequence and 2 bases overhang at the 3' end, were designed by Cenix and chemically synthesized by Ambion Inc., Austin, Tex., USA.

The following siRNA sequences were used:

```
scrambled negative control
5-AGUACUGCUUACGAUACGGTT-3  (SEQ ID NO. 21)
3-TTUCAUGACGAAUGCUAUGCC-5  (SEQ ID NO. 22)

positive control (PCNA,
proliferating cell nuclear antigen)
5-GGAGAAAGUUUCAGACUAUTT-3  (SEQ ID NO. 23)
3-GTCCUCUUUCAAAGUCUGAUA-5  (SEQ ID NO. 24)

NP_477517.1
5-GGGCUAUUGAGUGGCCAGATT-3  (SEQ ID NO. 25)
3-TTCCCGAUAACUCACCGGUCU-5  (SEQ ID NO. 26)

NP_001542.1
5-GGUGGAUUGAUAUCAGCUUTT-3  (SEQ ID NO. 27)
3-CTCCACCUAACUAUAGUCGAA-5  (SEQ ID NO. 28)
```

Transfection

HeLa cells were treated with siRNAs at a final concentration of 100 nM using a lipofection based transfection protocol.

24 h before transfection, HeLa cells were seeded in 96 well plates at a density of 6,000 cells/well.

On the day of transfection, the transfection mix was prepared as follows: 1 µl of a 10 µM stock of siRNA was diluted with 16 µl of Opti-MEM (Invitrogen Inc.), and 0.4 µl Oligofectamine transfection reagent (Invitrogen) were diluted with 2.4 µl of Opti-MEM. For complex formation, both solutions were gently mixed and incubated for 20 min at RT. Culture medium was removed from the cells and 80 µl of fresh medium (DMEM, Invitrogen) were added, followed by addition of 20 µl of transfection mix. Cells were incubated at 37° C. for 4 hours, 50 µl of fresh medium, supplemented with 30% fetal calf serum were added, followed by another incubation for 48-72 hours.

Determination of Silencing Level by Quantitative RT-PCR (qRT-PCR)

48 hours after transfection, total RNA was extracted from RNAi treated cells using Invisorb kits (Invitek GmbH, Berlin), and cDNA was produced with ABI TaqMan reverse transcription reagents (Applied Biosystems, USA). In both cases the manufacturer's instructions were followed. Quantitative real-time PCR was performed using the following protocol: 5.5 µl of 2× SybrGreen PCR mix (Applied Biosystems) were mixed with 3 µl of sample cDNA and 2.5 µl of a 2 µM solution of gene specific PCR primers, followed by incubation in a ABI-7900-HT real-time PCR machine at 50° C. 2 min-95° C. 10 min-45 cycles (95° C. 15 sec-60° C. 1 min)-95° C. 15 sec-60° C. 15 sec-95° C. 15 sec. In addition to the gene specific reaction, a second, reference reaction was run for each cDNA sample, using primers for 18S rRNA. Amplification signals from different gene specific samples were normalized using the reference values on 18S rRNA for these respective samples, and compared to samples from control (scrambled siRNA from Ambion Inc.) treated cells.

Proliferation Assay

In order to quantify the number of living cells after RNAi treatment, ATP levels were measured 72 h after transfection using the ATPlite assay (Perkin Elmer). Cells were extracted and treated according to the manufacturer's instructions. Luminescence read out was performed on a Victor 2 multi label reader (Perkin Elmer). For graphical presentation purposes the proliferation of untreated cells was set to 100.

Apoptosis Assay

The levels of programmed cell death in RNAi treated cells were determined 72 hours after transfection, using the Caspase 3/7 specific fluorometric assay ApoOne by Promega, following the manufacturer's instructions. Read out was performed on a Victor 2 multi label reader (Perkin Elmer). For graphical presentation purposes the apoptosis rate of untreated cells was set to 100.

Mitotic Index (MI)

Phosphorylation at serin 10 of histone H3 is considered a hallmark of mitosis, appearing in early prophase and disappearing during telophase. Using immunofluorescence microscopy, mitotic cells can be revealed by an increased binding of a phospho-histone H3 antibody, detected by a suitable fluorescence labelled secondary antibody.

RNAi treated cells in 96 well microscopy plates were stained using the following protocol: Cells were washed with PBS and fixed with 4% para-formaldehyde for 30 min at RT, followed by three washes with PBS. Cells were then permeabilised and blocked in the presence of 0.1% Triton X-100 and 2% BSA for 30 min. The supernatant was removed and anti Phospho Histone. H3 (mouse monoclonal antibody clone 6G3, Cell Signalling Technologies) was added at a dilution of 1:750 for 2 hours at RT, followed by three washes with PBS. For detection of Phosph Histone H3 labelled nuclei, goat anti mouse antibody (1:500), coupled to Alexa Fluor 568 (Molecular Probes) was added in a solution supplemented with 0.5 µg/ml Dapi (4',6-diamidino-2-phenylindole, dihydrochloride), FluoroPure™ grade, Molecular Probes) for detection of all nuclei. After incubation for 2 hours at RT, cells were washed four times and images were taken using an automated microscopy system (Discovery-1, Universal Imaging Inc.), acquiring a minimum of 6 images/well. Metamorph-HCS image processing software was used to determine the numbers of mitotic and overall nuclei. The Mitotic Index resembles the fraction of mitotic over all nuclei in a given cell population. For graphical presentation purposes the MI of untreated cells was set to 100.

Effects of RNAi Treatment

RNAi treatment of HeLa cells using an siRNA directed against NP_477517.1, the human ortholog of C. elegans gene F59E12.11, results in a 40% reduction of cell proliferation and a 2 fold increase in the rate of apoptosis. RNAi treatment of HeLa cells using an siRNA directed against NP_001542.1, the human ortholog of C. elegans gene Y71H2B.3, results in a 80% reduction of cell proliferation, a 2.5 fold increase in the rate of apoptosis, and a significant drop in the mitotic index.

The invention claimed is:

1. A method for the identification and characterization of drugs that inhibit or activate cell cycle progression, wherein the method comprises using a peptide or polypeptide molecule in a screening assay for the identification of said drug, and analyzing the cell cycle progression, wherein the peptide or polypeptide molecule comprises
   (a) a polypeptide sequence encoded by the nucleic acid sequence of SEQ ID NO: 3, or
   (b) the polypeptide sequence of SEQ ID NO: 4.

2. The method of claim 1, further comprising
   (a) transforming a nucleic acid molecule that encodes the peptide or polypeptide into a host cell or host organism,
   (b) cultivating the host cell or host organism under conditions that allow the overexpression of the peptide or polypeptide encoded by the nucleic acid molecule either in the presence or in the absence of at least one candidate for an inhibitor- or activator-molecule, and
   (c) analyzing the cell cycle progression in the cultivated cell or organism.

* * * * *

SEQUENCE LISTING

<160> NUMBER OF SEQ ID NOS: 28

<210> SEQ ID NO 1
<211> LENGTH: 936
<212> TYPE: DNA
<213> ORGANISM: Caenorhabditis elegans

<400> SEQUENCE: 1

```
atgtcgttcg tcccatcaga agttcgactt gatcacacat ttttagaacc gagattcaaa      60
ttccgcgcga gtttgagcca gatatcgaaa ccgacgcaat tcccaccatt gctcgtcagc     120
ccgccgaccc aaacactacc tggaacgaga ctggtttgga tcaaattcaa atgggaccaa     180
ccatcaatag tacaaaaaat taaatcaagg tttatgggaa cgaacaaag ctcgtcaaca      240
gcgggcacat catctaatcc tcaaaatcaa cagtcgtctt tttcatttct cactcgagcc     300
agtactaaac gatcaaaagg cattatcacg gtcaaagatg gcaatattcc tcaagaaaaa     360
ctcgaagatg atgaaattta caaaagattc accgaaattc ccgtttttt gccggtgatt      420
ccagccgtaa taggcaaacg agatccacaa acgaatcaag gagcttctta cactcatcaa     480
aaaatcagtt cgcggcccct ttttcgacta gcaacacgat tacaagaaca ttttgccgtt     540
aatgcgaaag cagtggcagc agatcaagct aaaattccag caacttgcaa gagtgttgaa     600
gcgaaaatga tcagacttat tgaagaaaca agagctcata agaacaaca tgacggtttt      660
atggctgcat tgagcggact taatcaattg cacgatgaca tctgtagtat tcagataatt     720
cttgaagata ttgtgccaat ggttgaaacg cttaatgaaa ttctaactcc cgacgaacgt     780
cttcctcctc ttaatcttgg ctcagtgctc gacagatctc ccgttccaag cagtgatagc     840
tcacttcaaa gtacgccccg ccataatcaa aatattggtc atattgatca aattgagccg     900
attgaagaaa tccgcgtagt tgatctacca aaataa                               936
```

<210> SEQ ID NO 2
<211> LENGTH: 240
<212> TYPE: PRT
<213> ORGANISM: Caenorhabditis elegans

<400> SEQUENCE: 2

Met Gly Asn Glu Gln Ser Ser Ser Thr Ala Gly Thr Ser Ser Asn Pro
1               5                   10                  15

Gln Asn Gln Gln Ser Ser Phe Ser Phe Leu Thr Arg Ala Ser Thr Lys
            20                  25                  30

Arg Ser Lys Gly Ile Ile Thr Val Lys Asp Gly Asn Ile Pro Gln Glu
        35                  40                  45

Lys Leu Glu Asp Asp Glu Ile Tyr Lys Arg Phe Thr Glu Ile Pro Arg
    50                  55                  60

Phe Leu Pro Val Ile Pro Ala Val Ile Gly Lys Arg Asp Pro Gln Thr
65                  70                  75                  80

Asn Gln Gly Ala Ser Tyr Thr His Gln Lys Ile Ser Ser Arg Pro Phe
                85                  90                  95

Phe Arg Leu Ala Thr Arg Leu Gln Glu His Phe Ala Val Asn Ala Lys
            100                 105                 110

Ala Val Ala Ala Asp Gln Ala Lys Ile Pro Ala Thr Cys Lys Ser Val
        115                 120                 125

Glu Ala Lys Met Ile Arg Leu Ile Glu Glu Thr Arg Ala His Lys Glu
    130                 135                 140

-continued

```
Gln His Asp Gly Phe Met Ala Ala Leu Ser Gly Leu Asn Gln Leu His
145                 150                 155                 160

Asp Asp Ile Cys Ser Ile Gln Ile Ile Leu Glu Asp Ile Val Pro Met
                165                 170                 175

Val Glu Thr Leu Asn Glu Ile Leu Thr Pro Asp Glu Arg Leu Pro Pro
            180                 185                 190

Leu Asn Leu Gly Ser Val Leu Asp Arg Ser Pro Val Pro Ser Ser Asp
        195                 200                 205

Ser Ser Leu Gln Ser Thr Pro Arg His Asn Gln Asn Ile Gly His Ile
    210                 215                 220

Asp Gln Ile Glu Pro Ile Glu Glu Ile Arg Val Val Asp Leu Pro Lys
225                 230                 235                 240
```

<210> SEQ ID NO 3
<211> LENGTH: 591
<212> TYPE: DNA
<213> ORGANISM: Homo sapiens

<400> SEQUENCE: 3

```
atgggcagtg agcagagctc cgaggccgag agccgaccca acgatctgaa ctcctcagtg    60
actccttcac cagccaagca tagagccaag atggatgata ttgtggttgt agctcagggc   120
tcccaggcct cacggaacgt cagcaacgat cccgatgtca tcaagttgca agagattcca   180
accttccagc ccctttgaa agggctattg agtggccaga cttccccaac aaatgccaaa   240
ttggagaaac tggactctca gcaggtgttg cagctctgcc tccgatatca agatcacctg   300
catcagtgtg cagaggccgt tgcttttgac cagaatgctt tggttaaacg aatcaaagag   360
atggatctgt ctgtagaaac tctgttcagc ttcatgcagg agcgccagaa agatacgcc   420
aagtatgccg agcagatcca gaaagtgaac gagatgtccg ccatcctccg ccgcatacag   480
atgggcatcg accagactgt gcccctgctg acaggctca acagcatgct gcccgagggc   540
gagcggctgg agcccttcag catgaagccc gaccgcgagc tcaggctgta g            591
```

<210> SEQ ID NO 4
<211> LENGTH: 196
<212> TYPE: PRT
<213> ORGANISM: Homo sapiens

<400> SEQUENCE: 4

```
Met Gly Ser Glu Gln Ser Ser Glu Ala Glu Ser Arg Pro Asn Asp Leu
1               5                   10                  15

Asn Ser Ser Val Thr Pro Ser Pro Ala Lys His Arg Ala Lys Met Asp
            20                  25                  30

Asp Ile Val Val Val Ala Gln Gly Ser Gln Ala Ser Arg Asn Val Ser
        35                  40                  45

Asn Asp Pro Asp Val Ile Lys Leu Gln Glu Ile Pro Thr Phe Gln Pro
    50                  55                  60

Leu Leu Lys Gly Leu Leu Ser Gly Gln Thr Ser Pro Thr Asn Ala Lys
65                  70                  75                  80

Leu Glu Lys Leu Asp Ser Gln Gln Val Leu Gln Leu Cys Leu Arg Tyr
                85                  90                  95

Gln Asp His Leu His Gln Cys Ala Glu Ala Val Ala Phe Asp Gln Asn
            100                 105                 110

Ala Leu Val Lys Arg Ile Lys Glu Met Asp Leu Ser Val Glu Thr Leu
        115                 120                 125

Phe Ser Phe Met Gln Glu Arg Gln Lys Arg Tyr Ala Lys Tyr Ala Glu
```

```
                130             135             140
Gln Ile Gln Lys Val Asn Glu Met Ser Ala Ile Leu Arg Arg Ile Gln
145                 150                 155                 160

Met Gly Ile Asp Gln Thr Val Pro Leu Leu Asp Arg Leu Asn Ser Met
                165                 170                 175

Leu Pro Glu Gly Glu Arg Leu Glu Pro Phe Ser Met Lys Pro Asp Arg
            180                 185                 190

Glu Leu Arg Leu
        195

<210> SEQ ID NO 5
<211> LENGTH: 984
<212> TYPE: DNA
<213> ORGANISM: Caenorhabditis elegans

<400> SEQUENCE: 5
atgtcagagc tatcagatga agaaatttcc ttgcaagcgc tttacgatcc gagcaaaaag      60
gtgatcggcg atattgaaga tgggattttt tccaccccgg agctccaacc tcgcatcaaa     120
acgggaattg ataatctcca gttggtcacg aagcttgtga atcagatgag attgttttcg     180
tcgaatgagc agattgaaga cgttccaaca aactcgctgc cctatctcct tgtcccatgt     240
tttttgggaa ttctccacca aaatttgatg actgagcccg gcctgaagct cgacgaactg     300
agaaaatcca aaatttatat gcgaaatttt ctggatcgcc tccgagattt gtgcctgatc     360
accaccagat taccatggga agatgaggat acagaagagc aaaatttaaa ggagaagccg     420
aagcttgcag ttgaagagat cagaagattg aagttggagc gtcacaagaa gaagcaagag     480
ctcaaaatgg cggagctcag gatccaaaag cagctggaag ccgtttcaat tgatgagcag     540
aatctcagag agctctatat tactcagtta ttgttctgga gtgaaagatg ttacgaggag     600
ttgcaggcga ttgatgacga gcttccactg ctgaaaatga tggctgaacg agcatctcac     660
ccacatcgtc atccagctcc accaccagca acaaagacag ttccaacact taaacccttc     720
attattacca gagatgctca acagaagcag gtctttgggc tcggatatcc aggaattcca     780
gcgatgagtg tcgatgaatg gtatcatcag aaattcggtc ataatccaca aaatgctcca     840
caatcgtcgg ctccagccgg ggcagaagct caagaatccg aagaagaggt tgatgatgac     900
gaggcgagag cgaaggcgat gcgttgggat gaatataagg atgatcatcg acgtggatgg     960
ggaaatatgc acaataaagg ataa                                             984

<210> SEQ ID NO 6
<211> LENGTH: 327
<212> TYPE: PRT
<213> ORGANISM: Caenorhabditis elegans

<400> SEQUENCE: 6

Met Ser Glu Leu Ser Asp Glu Glu Ile Ser Leu Gln Ala Leu Tyr Asp
1               5                   10                  15

Pro Ser Lys Lys Val Ile Gly Asp Ile Glu Asp Gly Ile Phe Ser Thr
            20                  25                  30

Pro Glu Leu Gln Pro Arg Ile Lys Thr Gly Ile Asp Asn Leu Gln Leu
        35                  40                  45

Val Thr Lys Leu Val Asn Gln Met Arg Leu Phe Ser Ser Asn Glu Gln
    50                  55                  60

Ile Glu Asp Val Pro Thr Asn Ser Leu Pro Tyr Leu Leu Val Pro Cys
65                  70                  75                  80
```

-continued

```
Phe Leu Gly Ile Leu His Gln Asn Leu Met Thr Glu Pro Gly Leu Lys
             85                  90                  95

Leu Asp Glu Leu Arg Lys Ser Lys Ile Tyr Met Arg Asn Phe Leu Asp
         100                 105                 110

Arg Leu Arg Asp Leu Cys Leu Ile Thr Thr Arg Leu Pro Trp Glu Asp
     115                 120                 125

Glu Asp Thr Glu Glu Gln Asn Leu Lys Glu Lys Pro Lys Leu Ala Val
 130                 135                 140

Glu Glu Ile Arg Arg Leu Lys Leu Glu Arg His Lys Lys Lys Gln Glu
145                 150                 155                 160

Leu Lys Met Ala Glu Leu Arg Ile Gln Lys Gln Leu Glu Ala Val Ser
                 165                 170                 175

Ile Asp Glu Gln Asn Leu Arg Glu Leu Tyr Ile Thr Gln Leu Leu Phe
             180                 185                 190

Trp Ser Glu Arg Cys Tyr Glu Glu Leu Gln Ala Ile Asp Asp Glu Leu
         195                 200                 205

Pro Leu Leu Lys Met Met Ala Glu Arg Ala Ser His Pro His Arg His
 210                 215                 220

Pro Ala Pro Pro Ala Thr Lys Thr Val Pro Thr Leu Lys Pro Phe
225                 230                 235                 240

Ile Ile Thr Arg Asp Ala Gln Gln Lys Gln Val Phe Gly Leu Gly Tyr
                 245                 250                 255

Pro Gly Ile Pro Ala Met Ser Val Asp Glu Trp Tyr His Gln Lys Phe
             260                 265                 270

Gly His Asn Pro Gln Asn Ala Pro Gln Ser Ser Ala Pro Ala Gly Ala
         275                 280                 285

Glu Ala Gln Glu Ser Glu Glu Val Asp Asp Glu Ala Arg Ala
 290                 295                 300

Lys Ala Met Arg Trp Asp Glu Tyr Lys Asp Asp His Arg Arg Gly Trp
305                 310                 315                 320

Gly Asn Met His Asn Lys Gly
                 325
```

<210> SEQ ID NO 7
<211> LENGTH: 1020
<212> TYPE: DNA
<213> ORGANISM: Homo sapiens

<400> SEQUENCE: 7

| | |
|---|---|
| atggctgctg aggacgagtt acagctgccg cggctccccg agctgttcga aactggtaga | 60 |
| cagttactgg acgaagtaga agtggcgact gaacccgccg gttcccggat agtccaggag | 120 |
| aaggtgttca agggcttgga cctccttgag aaggctgccg aaatgttatc gcagctcgac | 180 |
| ttgttcagcc gaaatgaaga tttggaagag attgcttcca ccgacctgaa gtacctttg | 240 |
| gtgccagcgt tcaaggagc cctcaccatg aaacaagtca accccagcaa gcgtctagat | 300 |
| catttgcagc gggctcgaga acactttata aactacttaa ctcagtgcca ttgctatcat | 360 |
| gtggcagagt tgagctgcc caaaaccatg aacaactctg ctgaaaatca cactgccaat | 420 |
| tcctccatgg cttatcctag tctcgttgct atggcatctc aaagacaggc taaaatacag | 480 |
| agatacaagc agaagaagga gttggagcat aggttgtctg caatgaaatc tgctgtggaa | 540 |
| agtggtcaag cagatgatga gcgtgttcgt gaatattatc ttcttcacct tcagaggtgg | 600 |
| attgatatca gcttagaaga gattgagagc attgaccagg aaataaagat cctgagagaa | 660 |
| agagactctt caagagaggc atcaacttct aactcatctc gccaggagag gcctccagtg | 720 |

```
aaacccttca ttctcactcg gaacatggct caagccaaag tatttggagc tggttatcca    780
agtctgccaa ctatgacggt gagtgactgg tatgagcaac atcggaaata tggagcatta    840
ccggatcagg gaatagccaa ggcagcacca gaggaattca gaaaagcagc tcagcaacag    900
gaagaacaag aagaaaagga ggaagaggat gatgaacaaa cactccacag agcccgggag    960
tgggatgact ggaaggacac ccatcctagg ggctatggga accgacagaa catgggctga   1020

<210> SEQ ID NO 8
<211> LENGTH: 339
<212> TYPE: PRT
<213> ORGANISM: Homo sapiens

<400> SEQUENCE: 8

Met Ala Ala Glu Asp Glu Leu Gln Leu Pro Arg Leu Pro Glu Leu Phe
1               5                   10                  15

Glu Thr Gly Arg Gln Leu Leu Asp Glu Val Glu Val Ala Thr Glu Pro
            20                  25                  30

Ala Gly Ser Arg Ile Val Gln Glu Lys Val Phe Lys Gly Leu Asp Leu
        35                  40                  45

Leu Glu Lys Ala Ala Glu Met Leu Ser Gln Leu Asp Leu Phe Ser Arg
    50                  55                  60

Asn Glu Asp Leu Glu Glu Ile Ala Ser Thr Asp Leu Lys Tyr Leu Leu
65                  70                  75                  80

Val Pro Ala Phe Gln Gly Ala Leu Thr Met Lys Gln Val Asn Pro Ser
                85                  90                  95

Lys Arg Leu Asp His Leu Gln Arg Ala Arg Glu His Phe Ile Asn Tyr
            100                 105                 110

Leu Thr Gln Cys His Cys Tyr His Val Ala Glu Phe Glu Leu Pro Lys
        115                 120                 125

Thr Met Asn Asn Ser Ala Glu Asn His Thr Ala Asn Ser Ser Met Ala
    130                 135                 140

Tyr Pro Ser Leu Val Ala Met Ala Ser Gln Arg Gln Ala Lys Ile Gln
145                 150                 155                 160

Arg Tyr Lys Gln Lys Lys Glu Leu Glu His Arg Leu Ser Ala Met Lys
                165                 170                 175

Ser Ala Val Glu Ser Gly Gln Ala Asp Asp Glu Arg Val Arg Glu Tyr
            180                 185                 190

Tyr Leu Leu His Leu Gln Arg Trp Ile Asp Ile Ser Leu Glu Glu Ile
        195                 200                 205

Glu Ser Ile Asp Gln Glu Ile Lys Ile Leu Arg Glu Arg Asp Ser Ser
    210                 215                 220

Arg Glu Ala Ser Thr Ser Asn Ser Ser Arg Gln Glu Arg Pro Pro Val
225                 230                 235                 240

Lys Pro Phe Ile Leu Thr Arg Asn Met Ala Gln Ala Lys Val Phe Gly
                245                 250                 255

Ala Gly Tyr Pro Ser Leu Pro Thr Met Thr Val Ser Asp Trp Tyr Glu
            260                 265                 270

Gln His Arg Lys Tyr Gly Ala Leu Pro Asp Gln Gly Ile Ala Lys Ala
        275                 280                 285

Ala Pro Glu Glu Phe Arg Lys Ala Ala Gln Gln Glu Glu Gln Glu
    290                 295                 300

Glu Lys Glu Glu Glu Asp Asp Glu Gln Thr Leu His Arg Ala Arg Glu
305                 310                 315                 320
```

Trp Asp Asp Trp Lys Asp Thr His Pro Arg Gly Tyr Gly Asn Arg Gln
            325                 330                 335

Asn Met Gly

<210> SEQ ID NO 9
<211> LENGTH: 1239
<212> TYPE: DNA
<213> ORGANISM: Rattus norvegicus

<400> SEQUENCE: 9

```
caagatggca gcgtctgaag aagagttact gctgccgcgg cttccggagc tcttcgaaac    60
cagcaagaaa cttctggagg agttggaagt agcaactgaa cccaccggct cccgaacaat   120
ccaggataag gtgtccaaag gactagaact ccttgagaag gctgccggaa tgttatcgca   180
gcttgatttg ttcagccgaa atgaagattt ggaagagatt gcttctatcg acctgaagta   240
cctgatggta ccagcgttgc aaggagctct caccatgaaa caagtcaacc ccagcaagcg   300
tctagatcat ttgcagcggg ctcgagaaca cttcatacat ttcttaactc agtgtcattg   360
ctatcatgtg gcagagtttc agctacccca aaccaagaat aactcagctg aaaataatac   420
tgctcgctcc tccatggcct atccaaatct cgttgctatg gcatctcaaa gacaggctaa   480
aatagagaga tacaagcaga gaaggaggt ggagcatagg ttgtctgcac tgaaatctgc   540
tgtggaaagt ggtcaagcag atgatgagcg tgttcgtgaa tattacctcc ttcaccttcg   600
gaggtggatt ggtatcagct agaagagat tgagagcatt gaccaggaaa taaagatcct   660
gaaagacaaa gactctccaa gagaggaatc agcttgtcag tcatctcttc cagagaagcc   720
tccaatgaaa cccttcatcc tcactcggaa caaggcacaa gccaaagtat ttggaactgg   780
ttatcccagc ctggcaacta tgacggtgag tgactggtat aacagcatc agaagtacgg   840
agccttacca gatcggggaa tagccaagcc gccatcagct gattttcaaa gagcagctca   900
gcagcaggaa gatcaagagc aaaaggatga agagaatgag gagaaagcct tgcacaggat   960
gcgagagtgg gatgactgga aggacacgca tcccaggggc tatggcaacc ggcagaacat  1020
gggctagtca ttccagaagg ccaaaggaca acgtggtgca caccttcaca ccaaggacaa  1080
cttcaggagg gtgcagtgag gcagccatg tggagtcttg cattgcattt gatagtgtca  1140
aataattgct tgtaccctag gtaatgacca gtgaattttt gtttggcttt attaatttca  1200
aaaaaaaaa aaaaaaaaa aaaaaaaaa aaaaaaaa                             1239
```

<210> SEQ ID NO 10
<211> LENGTH: 340
<212> TYPE: PRT
<213> ORGANISM: Rattus norvegicus

<400> SEQUENCE: 10

Met Ala Ala Ser Glu Glu Glu Leu Leu Leu Pro Arg Leu Pro Glu Leu
1               5                   10                  15

Phe Glu Thr Ser Lys Lys Leu Leu Glu Glu Leu Glu Val Ala Thr Glu
            20                  25                  30

Pro Thr Gly Ser Arg Thr Ile Gln Asp Lys Val Ser Lys Gly Leu Glu
        35                  40                  45

Leu Leu Glu Lys Ala Ala Gly Met Leu Ser Gln Leu Asp Leu Phe Ser
    50                  55                  60

Arg Asn Glu Asp Leu Glu Glu Ile Ala Ser Ile Asp Leu Lys Tyr Leu
65                  70                  75                  80

Met Val Pro Ala Leu Gln Gly Ala Leu Thr Met Lys Gln Val Asn Pro

|     |     |     |     |     |     |     |     | 85  |     |     |     |     | 90  |     |     |     |     | 95  |     |
| --- | --- | --- | --- | --- | --- | --- | --- | --- | --- | --- | --- | --- | --- | --- | --- | --- | --- | --- | --- |

Ser Lys Arg Leu Asp His Leu Gln Arg Ala Arg Glu His Phe Ile His
            100                    105                    110

Phe Leu Thr Gln Cys His Cys Tyr His Val Ala Glu Phe Gln Leu Pro
            115                    120                    125

Gln Thr Lys Asn Asn Ser Ala Glu Asn Asn Thr Ala Arg Ser Ser Met
130                        135                    140

Ala Tyr Pro Asn Leu Val Ala Met Ala Ser Gln Arg Gln Ala Lys Ile
145                    150                    155                    160

Glu Arg Tyr Lys Gln Lys Lys Glu Val Glu His Arg Leu Ser Ala Leu
            165                    170                    175

Lys Ser Ala Val Glu Ser Gly Gln Ala Asp Asp Glu Arg Val Arg Glu
            180                    185                    190

Tyr Tyr Leu Leu His Leu Arg Arg Trp Ile Gly Ile Ser Leu Glu Glu
            195                    200                    205

Ile Glu Ser Ile Asp Gln Glu Ile Lys Ile Leu Lys Asp Lys Asp Ser
210                        215                    220

Pro Arg Glu Glu Ser Ala Cys Gln Ser Ser Leu Pro Glu Lys Pro Pro
225                    230                    235                    240

Met Lys Pro Phe Ile Leu Thr Arg Asn Lys Ala Gln Ala Lys Val Phe
            245                    250                    255

Gly Thr Gly Tyr Pro Ser Leu Ala Thr Met Thr Val Ser Asp Trp Tyr
            260                    265                    270

Glu Gln His Gln Lys Tyr Gly Ala Leu Pro Arg Gly Ile Ala Lys
            275                    280                    285

Pro Pro Ser Ala Asp Phe Gln Arg Ala Ala Gln Gln Glu Asp Gln
290                    295                    300

Glu Gln Lys Asp Glu Glu Asn Glu Glu Lys Ala Leu His Arg Met Arg
305                    310                    315                    320

Glu Trp Asp Asp Trp Lys Asp Thr His Pro Arg Gly Tyr Gly Asn Arg
                    325                    330                    335

Gln Asn Met Gly
            340

<210> SEQ ID NO 11
<211> LENGTH: 1449
<212> TYPE: DNA
<213> ORGANISM: Drosophila melanogaster

<400> SEQUENCE: 11

```
atggctgagg gtaataccgc tggcggagag gaccaaaagc tgacggacat ctttctaaag      60
ggctggaaca tattcgacga gctagaagtt accgaactgc ccttcaatgg cagcgaattt     120
cagaacaaag tgaagactgc aatgggcctt ttcgagcagg ccaccgtcat tgtgaaccag     180
gttagcatgt tcagtgccaa cgagttgatc gacgaggtgt ccacggaatc gctaccattc     240
atgctgctcc cttactttct gggcaagctt accactaaga tcaacagccc aataacaca      300 cactccatag agctgggcga gatttacttc aaggaccacc tgcagcgttg ccaggagtat     360
gatctctgtg cagcgcccaa atctcaggtg gctaaggcgg atagccaagc ggaaaaaagc     420
gagcagcgcg agctggtaga ggcagccttc aatagaaacg acaaaatagc ccagtatcgc     480
cggatgaagg agattgacga gtatatggcc agaatgcgcg atgcagtcaa gaacaaaacg     540
gtcgacgatg aggataaacg tgtcttttc ctcaagtatt tggacaagag tataatagac     600
tccaagcagg aattagaaac attgggcgta atgaagcagc tggcccagat gcgccttgcc     660
```

-continued

```
cgattggctg gtggcgaatc cgacaacgaa gtggattcgt tccgtccacc gaatcaaaat    720
caatcttctg catcgtccac ctcccgcggt catggtcaca gccacggacc cggacaccac    780
caccatcatc agcaggccgc taagccaaag cccttgcagc ccttcatcat aacacgtaat    840
gccacccaga aggcggtttt cggcttggga tacccccagtt tgcccattat gactgttgat    900
gaattctacc agcagcgcgt cgacgagggc atctttcctg atgaggagaa ggttgccaag    960
atgaatcagg cacaggccat cgcggccgcc cgggatccca acgaaaaaga ggacgaggag   1020
aaggccgttg aggagctaca gcggagcag gatgatcccg agtatataga ccgcatgagg   1080
cgcatggatg aatacaagga tgtgcaaccc aaaagcagaa tgtcagtacg agactttatc   1140
aagggtctgc ccatacacga ttcgagcaat tttacccatt tgagcaacga acatggaatt   1200
cgaacgtcgc agaagcgtgc ctccgtctac ctgcccaccg aggatgagca ttcagagcag   1260
ctgatcgtga tggacaagcg atgtgtcctg ctgcgctacc tcactcagca gtgggacaaa   1320
aagacgcttc agcggaagag ggagcacggc ggcgattcgg gaaatggcaa cggcaacagc   1380
tccacgccca acggcaacag caccaacagc aaaaagcgcc cgcgcttgga ccccaacgag   1440
ctgaactga                                                           1449
```

<210> SEQ ID NO 12
<211> LENGTH: 482
<212> TYPE: PRT
<213> ORGANISM: Drosophila melanogaster

<400> SEQUENCE: 12

```
Met Ala Glu Gly Asn Thr Ala Gly Gly Glu Asp Gln Lys Leu Thr Asp
  1               5                  10                  15

Ile Phe Leu Lys Gly Trp Asn Ile Phe Asp Glu Leu Glu Val Thr Glu
             20                  25                  30

Leu Pro Phe Asn Gly Ser Glu Phe Gln Asn Lys Val Lys Thr Ala Met
         35                  40                  45

Gly Leu Phe Glu Gln Ala Thr Val Ile Val Asn Gln Val Ser Met Phe
     50                  55                  60

Ser Ala Asn Glu Leu Ile Asp Glu Val Ser Thr Glu Ser Leu Pro Phe
 65                  70                  75                  80

Met Leu Leu Pro Tyr Phe Leu Gly Lys Leu Thr Thr Lys Ile Asn Ser
                 85                  90                  95

Pro Asn Asn Thr His Ser Ile Glu Leu Gly Glu Ile Tyr Phe Lys Asp
            100                 105                 110

His Leu Gln Arg Cys Gln Glu Tyr Asp Leu Cys Ala Ala Pro Lys Ser
        115                 120                 125

Gln Val Ala Lys Ala Asp Ser Gln Ala Glu Lys Ser Glu Gln Arg Glu
    130                 135                 140

Leu Val Glu Ala Ala Phe Asn Arg Asn Asp Lys Ile Ala Gln Tyr Arg
145                 150                 155                 160

Arg Met Lys Glu Ile Asp Glu Tyr Met Ala Arg Met Arg Asp Ala Val
                165                 170                 175

Lys Asn Lys Thr Val Asp Asp Glu Asp Lys Arg Val Phe Phe Leu Lys
            180                 185                 190

Tyr Leu Asp Lys Ser Ile Ile Asp Ser Lys Gln Glu Leu Glu Thr Leu
        195                 200                 205

Gly Val Met Lys Gln Leu Ala Gln Met Arg Leu Ala Arg Leu Ala Gly
    210                 215                 220
```

```
Gly Glu Ser Asp Asn Glu Val Asp Ser Phe Arg Pro Pro Asn Gln Asn
225                 230                 235                 240

Gln Ser Ser Ala Ser Thr Ser Arg Gly His Gly His Ser His Gly
            245                 250                 255

Pro Gly His His His His His Gln Gln Ala Ala Lys Pro Lys Pro Leu
                260                 265                 270

Gln Pro Phe Ile Ile Thr Arg Asn Ala Thr Gln Lys Ala Val Phe Gly
            275                 280                 285

Leu Gly Tyr Pro Ser Leu Pro Ile Met Thr Val Asp Glu Phe Tyr Gln
            290                 295                 300

Gln Arg Val Asp Glu Gly Ile Phe Pro Asp Glu Lys Val Ala Lys
305                 310                 315                 320

Met Asn Gln Ala Gln Ala Ile Ala Ala Arg Asp Pro Asn Glu Lys
                325                 330                 335

Glu Asp Glu Glu Lys Ala Val Glu Glu Leu Gln Ala Glu Gln Asp Asp
                340                 345                 350

Pro Glu Tyr Ile Asp Arg Met Arg Arg Met Asp Glu Tyr Lys Asp Val
            355                 360                 365

Gln Pro Lys Ser Arg Met Ser Val Arg Asp Phe Ile Lys Gly Leu Pro
            370                 375                 380

Ile His Asp Ser Ser Asn Phe Thr His Leu Ser Asn Glu His Gly Ile
385                 390                 395                 400

Arg Thr Ser Gln Lys Arg Ala Ser Val Tyr Leu Pro Thr Glu Asp Glu
                405                 410                 415

His Ser Glu Gln Leu Ile Val Met Asp Lys Arg Cys Val Leu Leu Arg
                420                 425                 430

Tyr Leu Thr Gln Gln Trp Asp Lys Lys Thr Leu Gln Arg Lys Arg Glu
            435                 440                 445

His Gly Gly Asp Ser Gly Asn Gly Asn Gly Asn Ser Ser Thr Pro Asn
                450                 455                 460

Gly Asn Ser Thr Asn Ser Lys Lys Arg Pro Arg Leu Asp Pro Asn Glu
465                 470                 475                 480

Leu Asn

<210> SEQ ID NO 13
<211> LENGTH: 1101
<212> TYPE: DNA
<213> ORGANISM: Saccharomyces cerevisiae

<400> SEQUENCE: 13
atggcgtcag taacagaaca attcaacgat attattagct tatactcaac aaaattggaa      60
cacacatctt tgaggcaaga ttcaccagag taccaggat tattactttc cacgatcaag      120
aaattattaa acttaaaaac agcaattttt gacaggttgg cattgttcag tactaatgag      180
accattgatg atgtgtctac tgcttccatc aaatttctag cagttgatta ctatttagga      240
ttattgatat caagacgaca gtcgaatgat tcggatgttg ctcaaaggca gtctatgaaa      300
ttgatttacc tgaaaaaaag cgttgaatct ttcattaatt tcctgacact attgcaggat      360
tataagcttc tagatccttt ggttggtgaa aaactaggta acttcaagga tcgttataac      420
cctcagctta gcgaattgta cgcgcaacca aaaaataaca aagatttatc tggagcacag      480
ttgaagagaa agaaaagat tgagctattc cagcgcaata agaaattag cacaaaactg      540 cactgcttgg agttggaatt aaaaaacaac gacgaggacc acgaccatga tgaattacta      600
agagaactat atttgatgag gttacatcac tttagtcttg atacgattaa caacattgaa      660
```

-continued

```
cagaatttat tgaatgtga aatgctctct aatttcctca aaaattccgt acatgaagtc      720
aaatcatcag gtactcagat acgaaaagaa tcgaatgatg atgattccac tggttttacc      780
gataaattag agaatataaa taagccattg atagacaaaa aaggtcaagt cttgaggaac      840
ttcacgcttg tcgacaaaag gcaacaactg caacaaaaag tgcgaggata tggtcaatat      900
ggaccaacaa tgtcggtgga ggattttta gataaagagt ttgaagaagg tcgcgttctt      960
caaggtggcg aagaaccaga gcaagcacca gatgaagaaa acatggactg caagataga     1020 gaaacctata agctcgtga gtgggacgag ttcaaggaaa gtcatgctaa gggaagcgga     1080
aataccatga atagaggata g                                               1101
```

<210> SEQ ID NO 14
<211> LENGTH: 366
<212> TYPE: PRT
<213> ORGANISM: Saccharomyces cerevisiae

<400> SEQUENCE: 14

```
Met Ala Ser Val Thr Glu Gln Phe Asn Asp Ile Ile Ser Leu Tyr Ser
1               5                   10                  15

Thr Lys Leu Glu His Thr Ser Leu Arg Gln Asp Ser Pro Glu Tyr Gln
            20                  25                  30

Gly Leu Leu Ser Thr Ile Lys Lys Leu Leu Asn Leu Lys Thr Ala
        35                  40                  45

Ile Phe Asp Arg Leu Ala Leu Phe Ser Thr Asn Glu Thr Ile Asp Asp
    50                  55                  60

Val Ser Thr Ala Ser Ile Lys Phe Leu Ala Val Asp Tyr Tyr Leu Gly
65                  70                  75                  80

Leu Leu Ile Ser Arg Arg Gln Ser Asn Asp Ser Asp Val Ala Gln Arg
                85                  90                  95

Gln Ser Met Lys Leu Ile Tyr Leu Lys Lys Ser Val Glu Ser Phe Ile
            100                 105                 110

Asn Phe Leu Thr Leu Leu Gln Asp Tyr Lys Leu Leu Asp Pro Leu Val
        115                 120                 125

Gly Glu Lys Leu Gly Asn Phe Lys Asp Arg Tyr Asn Pro Gln Leu Ser
    130                 135                 140

Glu Leu Tyr Ala Gln Pro Lys Asn Asn Lys Asp Leu Ser Gly Ala Gln
145                 150                 155                 160

Leu Lys Arg Lys Glu Lys Ile Glu Leu Phe Gln Arg Asn Lys Glu Ile
                165                 170                 175

Ser Thr Lys Leu His Cys Leu Glu Leu Glu Leu Lys Asn Asn Asp Glu
            180                 185                 190

Asp His Asp His Asp Glu Leu Leu Arg Glu Leu Tyr Leu Met Arg Leu
        195                 200                 205

His His Phe Ser Leu Asp Thr Ile Asn Asn Ile Glu Gln Asn Leu Phe
    210                 215                 220

Glu Cys Glu Met Leu Ser Asn Phe Leu Lys Asn Ser Val His Glu Val
225                 230                 235                 240

Lys Ser Ser Gly Thr Gln Ile Arg Lys Glu Ser Asn Asp Asp Ser
                245                 250                 255

Thr Gly Phe Thr Asp Lys Leu Glu Asn Ile Asn Lys Pro Leu Ile Asp
            260                 265                 270

Lys Lys Gly Gln Val Leu Arg Asn Phe Thr Leu Val Asp Lys Arg Gln
        275                 280                 285
```

-continued

```
Gln Leu Gln Gln Lys Val Arg Gly Tyr Gly Gln Tyr Gly Pro Thr Met
    290                 295                 300

Ser Val Glu Glu Phe Leu Asp Lys Glu Phe Glu Glu Gly Arg Val Leu
305                 310                 315                 320

Gln Gly Gly Glu Glu Pro Glu Gln Ala Pro Asp Glu Glu Asn Met Asp
                325                 330                 335

Trp Gln Asp Arg Glu Thr Tyr Lys Ala Arg Glu Trp Asp Glu Phe Lys
            340                 345                 350

Glu Ser His Ala Lys Gly Ser Gly Asn Thr Met Asn Arg Gly
        355                 360                 365

<210> SEQ ID NO 15
<211> LENGTH: 19
<212> TYPE: DNA
<213> ORGANISM: Unknown
<220> FEATURE:
<223> OTHER INFORMATION: T7 polymerase promoter sequence

<400> SEQUENCE: 15
taatacgact cactatagg                                               19

<210> SEQ ID NO 16
<211> LENGTH: 19
<212> TYPE: DNA
<213> ORGANISM: Unknown
<220> FEATURE:
<223> OTHER INFORMATION: T3 polymerase promoter sequence

<400> SEQUENCE: 16
aattaaccct cactaaagg                                               19

<210> SEQ ID NO 17
<211> LENGTH: 39
<212> TYPE: DNA
<213> ORGANISM: Unknown
<220> FEATURE:
<223> OTHER INFORMATION: Forward PCR primer for in vitro dsRNA synthesis

<400> SEQUENCE: 17
taatacgact cactataggg gatttcttca atcggctca                         39

<210> SEQ ID NO 18
<211> LENGTH: 39
<212> TYPE: DNA
<213> ORGANISM: Unknown
<220> FEATURE:
<223> OTHER INFORMATION: Reverse PCR primer for in vitro dsRNA synthesis

<400> SEQUENCE: 18
aattaaccct cactaaaggt atgtcgttcg tcccatcag                         39

<210> SEQ ID NO 19
<211> LENGTH: 39
<212> TYPE: DNA
<213> ORGANISM: Unknown
<220> FEATURE:
<223> OTHER INFORMATION: Forward PCR primer for in vitro dsRNA synthesis

<400> SEQUENCE: 19
taatacgact cactataggt gcgaaacctg aattttttcc                        39

<210> SEQ ID NO 20
<211> LENGTH: 39
<212> TYPE: DNA
```

```
<213> ORGANISM: Unknown
<220> FEATURE:
<223> OTHER INFORMATION: Reverse PCR primer for in vitro dsRNA synthesis

<400> SEQUENCE: 20
aattaaccct cactaaaggg ctcatcaatt gaaacggct                    39

<210> SEQ ID NO 21
<211> LENGTH: 21
<212> TYPE: DNA
<213> ORGANISM: Unknown
<220> FEATURE:
<223> OTHER INFORMATION: siRNA sequence for scrambled negative control
      (first strand)

<400> SEQUENCE: 21
aguacugcuu acgauacggt t                                       21

<210> SEQ ID NO 22
<211> LENGTH: 21
<212> TYPE: DNA
<213> ORGANISM: Unknown
<220> FEATURE:
<223> OTHER INFORMATION: siRNA sequence for scrambled negative control
(second strand)

<400> SEQUENCE: 22
ccguaucgua agcaguacut t                                       21

<210> SEQ ID NO 23
<211> LENGTH: 21
<212> TYPE: DNA
<213> ORGANISM: Unknown
<220> FEATURE:
<223> OTHER INFORMATION: siRNA sequence for positive control (PCNA,
      proliferating cell nuclear antigen) (first strand)

<400> SEQUENCE: 23
ggagaaaguu ucagacuaut t                                       21

<210> SEQ ID NO 24
<211> LENGTH: 21
<212> TYPE: DNA
<213> ORGANISM: Unknown
<220> FEATURE:
<223> OTHER INFORMATION: siRNA sequence for positive control (PCNA,
      proliferating cell nuclear antigen) (second strand)

<400> SEQUENCE: 24
auagucugaa acuuucucct g                                       21

<210> SEQ ID NO 25
<211> LENGTH: 21
<212> TYPE: DNA
<213> ORGANISM: Unknown
<220> FEATURE:
<223> OTHER INFORMATION: siRNA sequence for NP_477517.1 (first strand)

<400> SEQUENCE: 25
gggcuauuga guggccagat t                                       21

<210> SEQ ID NO 26
<211> LENGTH: 21
<212> TYPE: DNA
<213> ORGANISM: Unknown
<220> FEATURE:
<223> OTHER INFORMATION: siRNA sequence for NP_477517.1 (second strand)
```

```
<400> SEQUENCE: 26
ucuggccacu caauagccct t                                              21

<210> SEQ ID NO 27
<211> LENGTH: 21
<212> TYPE: DNA
<213> ORGANISM: Unknown
<220> FEATURE:
<223> OTHER INFORMATION: siRNA sequence for NP_001542.1 (first strand)

<400> SEQUENCE: 27
gguggauuga uaucagcuut t                                              21

<210> SEQ ID NO 28
<211> LENGTH: 21
<212> TYPE: DNA
<213> ORGANISM: Unknown
<220> FEATURE:
<223> OTHER INFORMATION: siRNA sequence for NP_001542.1 (second strand)

<400> SEQUENCE: 28
aagcugauau caauccacct c                                              21
```